US012616841B2

(12) United States Patent
Schilling et al.

(10) Patent No.: US 12,616,841 B2
(45) Date of Patent: May 5, 2026

(54) IMPLANTABLE MEDICAL DEVICE FOR DETECTING ACOUSTIC COMMUNICATION SIGNALS AND ACOUSTIC BIOMETRIC SIGNALS

(71) Applicant: Medtronic, Inc., Minneapolis, MN (US)

(72) Inventors: Eric A. Schilling, Ham Lake, MN (US); Xusheng Zhang, Shoreview, MN (US)

(73) Assignee: Medtronic, Inc., Minneapolis, MN (US)

( * ) Notice: Subject to any disclaimer, the term of this patent is extended or adjusted under 35 U.S.C. 154(b) by 215 days.

(21) Appl. No.: 18/510,129

(22) Filed: Nov. 15, 2023

(65) Prior Publication Data
US 2024/0245921 A1    Jul. 25, 2024

Related U.S. Application Data

(60) Provisional application No. 63/481,079, filed on Jan. 23, 2023.

(51) Int. Cl.
| | |
|---|---|
| *A61N 1/372* | (2006.01) |
| *A61N 1/02* | (2006.01) |
| *A61N 1/39* | (2006.01) |
| *G10L 25/51* | (2013.01) |

(52) U.S. Cl.
CPC ......... *A61N 1/37217* (2013.01); *A61N 1/025* (2013.01); *A61N 1/3956* (2013.01); *A61N 1/3975* (2013.01); *A61N 1/3987* (2013.01); *G10L 25/51* (2013.01)

(58) Field of Classification Search
CPC ... A61N 1/37217; A61N 1/025; A61N 1/3956
USPC ............................................................. 607/7
See application file for complete search history.

(56) References Cited

U.S. PATENT DOCUMENTS

| | | | |
|---|---|---|---|
| 6,236,889 B1 | 5/2001 | Soykan et al. | |
| 8,078,285 B2 | 12/2011 | Ganion et al. | |
| 8,301,262 B2 | 10/2012 | Mi et al. | |
| 8,369,960 B2 | 2/2013 | Tran et al. | |
| 8,594,802 B2 | 11/2013 | Stahmann et al. | |
| 8,626,296 B2 | 1/2014 | Von Arx et al. | |

(Continued)

FOREIGN PATENT DOCUMENTS

WO        2013080038 A2    6/2013

*Primary Examiner* — Nadia A Mahmood
(74) *Attorney, Agent, or Firm* — Shumaker & Sieffert, P.A.

(57) ABSTRACT

In some examples, a medical device system includes an implantable medical device (IMD) configured to be implanted underneath a skin of a patient, the IMD comprising: acoustic receiving circuitry configured to: receive one or more acoustic communication signals; and receive one or more acoustic biometric signals from the patient. The medical device system includes communication circuitry configured for wireless communication according to a communication protocol. Additionally, the medical device system includes processing circuitry configured to: receive, via the acoustic receiving circuitry, a sequence of acoustic communication signals that are separate from the one or more acoustic biometric signals; decode the sequence of acoustic communication signals to identify one or more requested actions; and control the IMD to perform the one or more requested actions.

20 Claims, 8 Drawing Sheets

(56)                    References Cited

U.S. PATENT DOCUMENTS

| | | | |
|---|---|---|---|
| 9,468,767 | B2 | 10/2016 | Hill et al. |
| 9,492,671 | B2 | 11/2016 | O'Brien et al. |
| 9,998,237 | B2 | 6/2018 | Moss |
| 2008/0108915 | A1* | 5/2008 | Penner ............... A61N 1/37217 |
| | | | 600/16 |
| 2010/0023091 | A1 | 1/2010 | Stahmann et al. |
| 2010/0249882 | A1 | 9/2010 | Houben |
| 2014/0012342 | A1 | 1/2014 | Penner et al. |
| 2021/0128014 | A1 | 5/2021 | Arneson et al. |

* cited by examiner

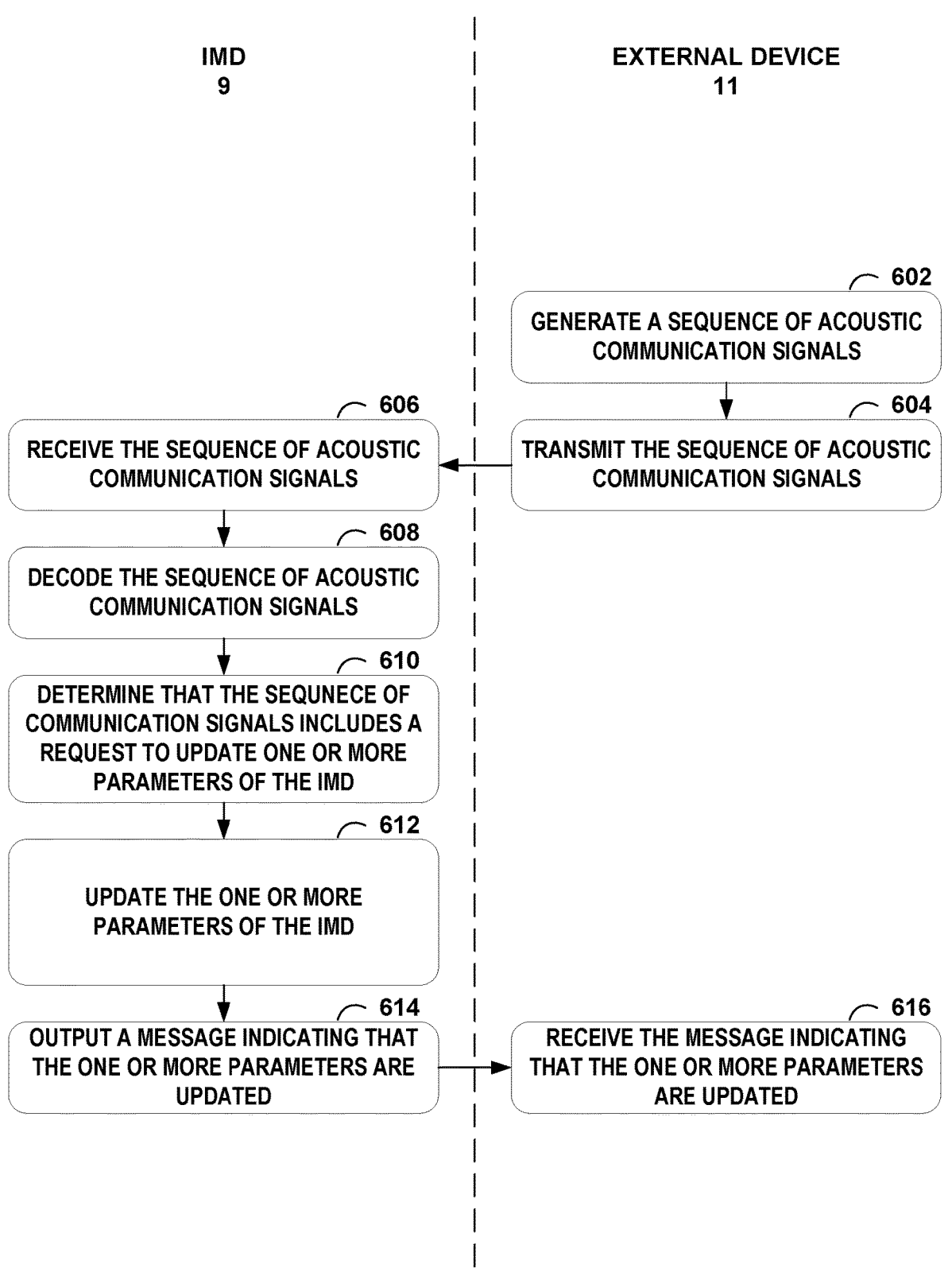

IMD
9

EXTERNAL DEVICE
11

602

GENERATE A SEQUENCE OF ACOUSTIC
COMMUNICATION SIGNALS

606

RECEIVE THE SEQUENCE OF ACOUSTIC
COMMUNICATION SIGNALS

604

TRANSMIT THE SEQUENCE OF ACOUSTIC
COMMUNICATION SIGNALS

608

DECODE THE SEQUENCE OF ACOUSTIC
COMMUNICATION SIGNALS

610

DETERMINE THAT THE SEQUNECE OF
COMMUNICATION SIGNALS INCLUDES A
REQUEST TO UPDATE ONE OR MORE
PARAMETERS OF THE IMD

612

UPDATE THE ONE OR MORE
PARAMETERS OF THE IMD

614

OUTPUT A MESSAGE INDICATING THAT
THE ONE OR MORE PARAMETERS ARE
UPDATED

616

RECEIVE THE MESSAGE INDICATING
THAT THE ONE OR MORE PARAMETERS
ARE UPDATED

FIG. 6

IMPLANTABLE MEDICAL DEVICE FOR DETECTING ACOUSTIC COMMUNICATION SIGNALS AND ACOUSTIC BIOMETRIC SIGNALS

This application claims the benefit of U.S. Provisional Patent Application No. 63/481,079, filed on Jan. 23, 2023, the entire content of which is incorporated herein by reference.

TECHNICAL FIELD

The present application relates to implantable medical devices and, more particularly, implantable medical devices configured to communicate wirelessly with one or more other devices.

BACKGROUND

Implantable medical devices (IMDs) may be surgically implanted in a patient to monitor one or more physiological parameters of the patient and/or deliver therapy to suppress one or more symptoms of the patient. For example, an IMD may include a cardiac monitor, be configured to deliver cardiac pacing or another electrical therapy to the patient, and/or be configured to terminate tachyarrhythmia by delivery of high energy shocks. A clinician or patient may use an external device to retrieve information collected by the IMD and/or to configure or adjust one or more parameters of the monitoring and/or therapy provided by the IMD. Typically, the external device connects to the IMD via a wireless connection. In some examples, a wireless connection is established between the external device and the IMD using a Bluetooth® wireless protocol. In such an example, the external device may be treated as a central device, and one or more IMDs are treated as peripheral devices.

In some examples, IMDs may include acoustic circuitry configured to sense one or more physiological acoustic signals. Processing circuitry may analyze the one or more physiological acoustic signals to monitor one or more patient conditions and/or determine one or more therapy parameters. For example, physiological acoustic signals may include heart sounds that indicate one or more parameters of the patient's cardiac function.

SUMMARY

In general, the disclosure is directed to devices, systems, and techniques for communicating with an implantable medical device (IMD) via acoustic circuitry when communication circuitry of the IMD is disabled, offline, powered down, or otherwise unable to send and receive communications. For example, the IMD may be configured to communicate with one or more other devices via the communication circuitry according to a communication protocol (e.g., a Bluetooth® wireless protocol). Since communication circuitry may draw a considerable amount of energy, it may be beneficial to transition communication circuitry to an offline mode or a low-power mode when the communication circuitry is not in use. But when the communication circuitry is offline or in a low-power mode, other devices might not be able to communicate with the IMD via the communication circuitry according to the communication protocol. One or more techniques described herein may include transmitting and/or receiving one or more acoustic messages via acoustic circuitry of the IMD, thus enabling communication even when the communication circuitry is not in use.

In some examples, it may be beneficial for an IMD to be small in size. Smaller IMDs may require less invasive implant procedures and cause less discomfort to the patient as compared with larger IMDs, but smaller IMDs have less room for communication circuitry as compared with larger IMDs. This means that while a larger IMD may include separate communication circuitry configured for "waking up" main communication circuitry according to a proprietary communication protocol and/or communicating with the device while the main communication circuitry is offline, a smaller IMD might not include separate communication circuitry. An IMD may include one or more sensors (e.g., electrodes, accelerometers, optical sensors, acoustic sensors) configured to collect patient data for analysis. One or more of these sensors may be configured to sense signals from sources that are separate from patient physiological signals. For example, the one or more sensors may detect communication signals from another device. Additionally, or alternatively, the one or more other sensors may detect signals from other sources, such as a human voice (e.g., the patient's voice).

The techniques of this disclosure may provide one or more advantages. For example, an IMD may include communication circuitry configured to communicate with one or more other devices according to a communication protocol, but the IMD may transition the communication circuitry to an offline mode or a low-power mode in some cases to preserve energy and extend a longevity of a power source of the IMD. This means that it might not be possible for the IMD to communicate according to the communication protocol while the communication circuitry is offline. The IMD may include acoustic receiving circuitry that is configured to detect one or more acoustic biometric signals of the patient (e.g., heart sounds). The acoustic receiving circuitry is also configured to receive acoustic communication signals, meaning that the IMD may receive communications from external sources even when the communication circuitry is offline or in low power mode. The IMD may in some cases, receive acoustic communications from external devices and/ or receive one or more acoustic communication signals from a living source (e.g., a human voice). By including acoustic receiving circuitry that is configured to detect both acoustic communication signals and acoustic biometric signals, the IMD may more efficiently communicate while the communication circuitry is offline as compared with devices that receive signals via secondary communication circuitry while primary communication circuitry is offline. Using acoustic receiving circuitry extends a battery longevity of the IMD by allowing the IMD to power down the communication circuitry while the communication circuitry is not in use, and activate the communication circuitry in response to receiving acoustic communications. The acoustic receiving circuitry also provides the IMD with a secondary mode of communication that does not require additional circuitry that is not used for sensing biometric signals, thus preventing the IMD from requiring components which increase its size.

The IMD may in some examples, include acoustic transmission circuitry configured to output one or more acoustic signals. The acoustic transmission circuitry may in some examples, include one or more components that are also part of the acoustic receiving circuitry. By using acoustic transmission circuitry to send communications while the communication circuitry is disabled or powered down, the IMD may send communications even when communication circuitry is offline. In general, using acoustic circuitry to send and receive communication signals while communication circuitry is offline may provide the IMD with a secondary mode of communication that takes less space with the IMD as compared with medical devices that use separate communication circuitry not configured to sense biometric signals. This means that the IMD may be smaller as compared with medical devices that use separate communication circuitry.

In one example, a medical device system includes an IMD configured to be implanted underneath a skin of a patient, the IMD comprising: acoustic receiving circuitry configured to: receive one or more acoustic communication signals; and receive one or more acoustic biometric signals from the patient. The IMD also includes communication circuitry configured for wireless communication according to a communication protocol. The medical device system also includes processing circuitry configured to: receive, via the acoustic receiving circuitry, a sequence of acoustic communication signals of the one or more acoustic communication signals that are separate from the one or more acoustic biometric signals; decode the sequence of acoustic communication signals to identify one or more requested actions; and control the IMD to perform the one or more requested actions.

In another example, a method includes receiving, by processing circuitry via acoustic receiving circuitry, a sequence of acoustic communication signals of one or more acoustic communication signals that are separate from one or more acoustic biometric signals, wherein an IMD configured to be implanted underneath a skin of a patient comprises the acoustic receiving circuitry configured to receive the one or more acoustic communication signals and receive the one or more acoustic biometric signals from the patient, and wherein the IMD comprises communication circuitry configured for wireless communication according to a communication protocol. The method also includes decoding, by the processing circuitry, the sequence of acoustic communication signals to identify one or more requested actions; and controlling, by the processing circuitry, the IMD to perform the one or more requested actions.

In another example, a non-transitory computer-readable medium includes instructions for causing one or more processors to: receive, via acoustic receiving circuitry, a sequence of acoustic communication signals of one or more acoustic communication signals that are separate from one or more acoustic biometric signals, wherein an IMD configured to be implanted underneath a skin of a patient comprises the acoustic receiving circuitry configured to receive the one or more acoustic communication signals and receive the one or more acoustic biometric signals from the patient, and wherein the IMD comprises communication circuitry configured for wireless communication according to a communication protocol. The instructions also cause the one or more processors to decode the sequence of acoustic communication signals to identify one or more requested actions; and control the IMD to perform the one or more requested actions.

This summary is intended to provide an overview of the subject matter described in this disclosure. It is not intended to provide an exclusive or exhaustive explanation of the systems, devices, and methods described in detail within the accompanying drawings and description below. Further details of one or more examples are set forth in the accompanying drawings and the description below. Other features, objects, and advantages will be apparent from the description and drawings, and from the statements provided below.

BRIEF DESCRIPTION OF DRAWINGS

FIG. 6 is a flow diagram illustrating an example operation for updating one or more parameters, in accordance with one or more techniques of this disclosure.

DETAILED DESCRIPTION

Figure 1A:
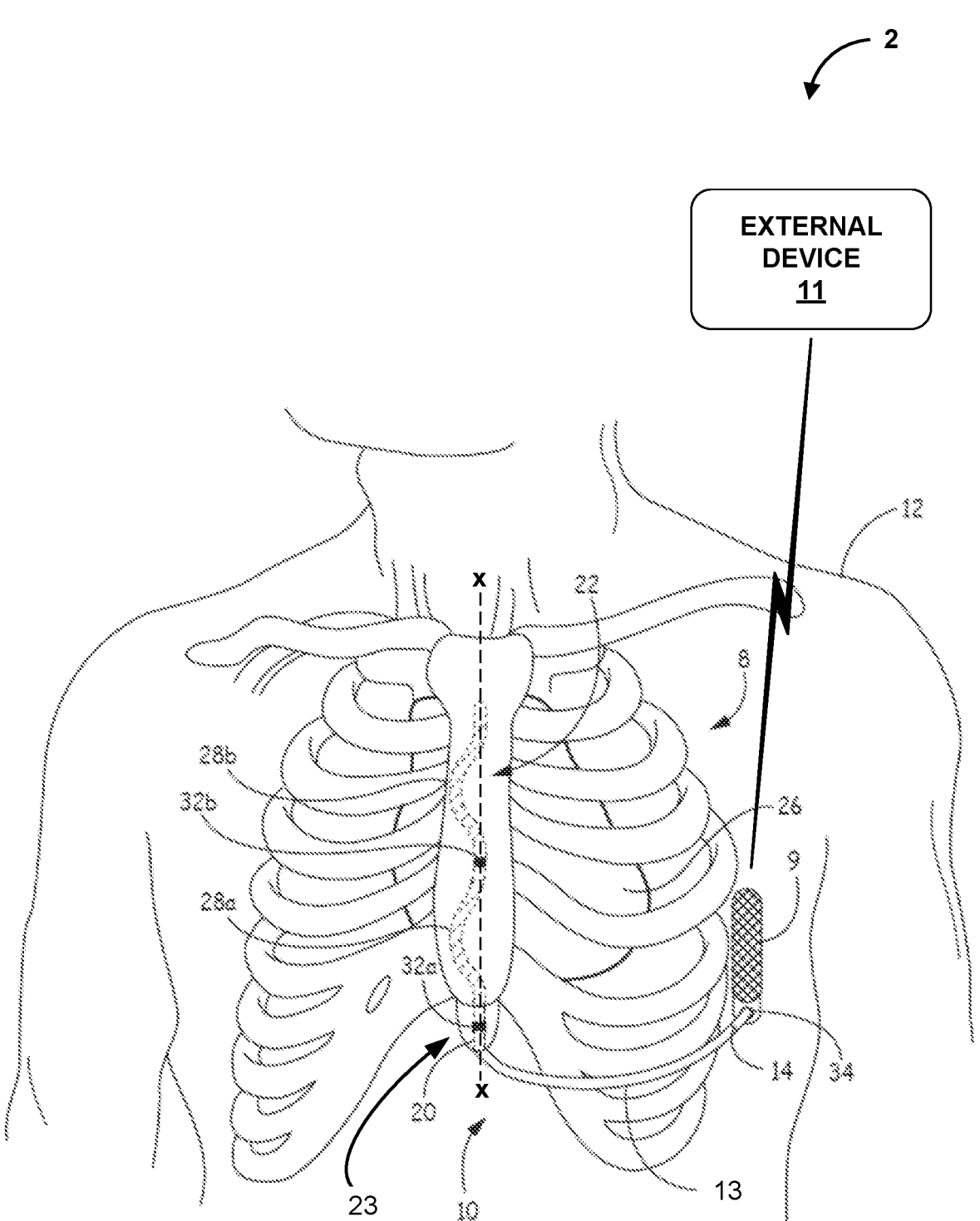
FIGS. 1A-1C are conceptual diagrams illustrating an example medical device system including an implantable cardioverter defibrillator (ICD) system, in accordance with one or more techniques of this disclosure.

This disclosure describes techniques for establishing communication by a medical device. In some examples, communication is established between at least one implantable medical device (IMD) and at least one external device. An external device may for example, transmit a signal to the IMD in order initiate a communication link with the IMD, request data from the IMD, instruct the IMD to update one or more parameters of the IMD, or any combination thereof. However, the techniques of this disclosure are not limited to implantable devices or medical devices. The techniques may be used by any device to communicate with other entities. The techniques of this disclosure are also not limited to communication between the IMD and other devices. In some examples, an IMD may receive communications from a non-device source (e.g., receive human voice audio signals).

In some examples, an IMD records one or more physiological signals of a patient, where the one or more physiological signals may be indicative of a medical condition. The IMD may use any combination of electrodes, chemical sensors, temperature sensors, acoustic sensors, motion sensors, optical sensors, or other sensors to sense the physiological signals and store data indicative of the physiological signals in a memory. In some examples, the IMD delivers therapy, such as cardiac pacing or anti-tachyarrhythmia shocks, and stores data indicative of the therapy delivered. In some examples, the IMD records patient data without delivering therapy. In some examples, the IMD stores data regarding the status and performance of the IMD and components thereof, and operational parameters that control the functioning of the IMD, e.g., for sensing and/or delivering therapy.

Since the IMD is implanted within the patient, in some cases, the IMD may wirelessly communicate with an external device, e.g., to transmit at least some patient data to an external device for analysis by a clinician. Additionally, a user (e.g., the patient or the clinician) may provide user input to an external device to control the IMD. The external device may in turn transmit instructions to the IMD based on the user input. Since the IMD consumes power when it communicates with other devices, it may be beneficial to limit an amount of power that the IMD consumes for communication in order to preserve a power level of the IMD. For example, IMD may transition communication circuitry to an offline mode or a low-power mode when it is not in use. IMD may transition the communication circuitry to a high-power mode in order to establish a communication link.

Some IMDs may communicate with external devices that are manufactured by the manufacturer of the IMD, but this is not necessary. In some examples, consumer electronic devices (e.g., tablets, computers, smart phones) may execute an application for communicating with an IMD in order to control the IMD, program one or more parameters of the IMD, send information to the IMD, request information from the IMD, or any combination thereof. It may be beneficial for an external device to use one or more communication protocols (e.g., Bluetooth® communication protocols) to communicate with the IMD, because consumer electronic devices may include communication circuitry such as a Bluetooth® radios for communicating according to one or more communication protocols. According to one or more techniques described herein, an IMD may include a communication circuitry such as a Bluetooth® radio in order to facilitate communication with consumer electronic external devices according to a primary mode of communication (e.g., a Bluetooth® communication protocol). But in some cases, the primary mode of communication may fail or be offline, preventing an external device from communicating with the IMD according to the primary mode of communication.

The external device may in some examples, communicate with the IMD according to a secondary mode of communication. For example, the secondary mode of communication may include acoustic communication. The external device and/or the IMD may receive and/or send one or more acoustic communication signals. Since the IMD may include acoustic circuitry for detecting one or more acoustic physiological signals, the IMD may use the same acoustic circuitry for detecting acoustic communication signals sent by the external device. This means that the IMD may be configured to receive acoustic communication signals from the external device as a secondary mode of communication using acoustic circuitry that is already within IMD and configured for another purpose, to sense acoustic physiological signals of the patient. In other words, it might not be necessary for the IMD to include separate communication circuitry for communicating with the external device according to one or more secondary communication protocols when Bluetooth® communication is offline. In some examples, the term "acoustic communication signal" may refer to any acoustic signal sent from another device and/or sound from a human source (e.g., a human voice). In some examples, a signal received by the IMD to "wake up" communication circuitry of the IMD may represent an acoustic communication signal.

Figure 1B:
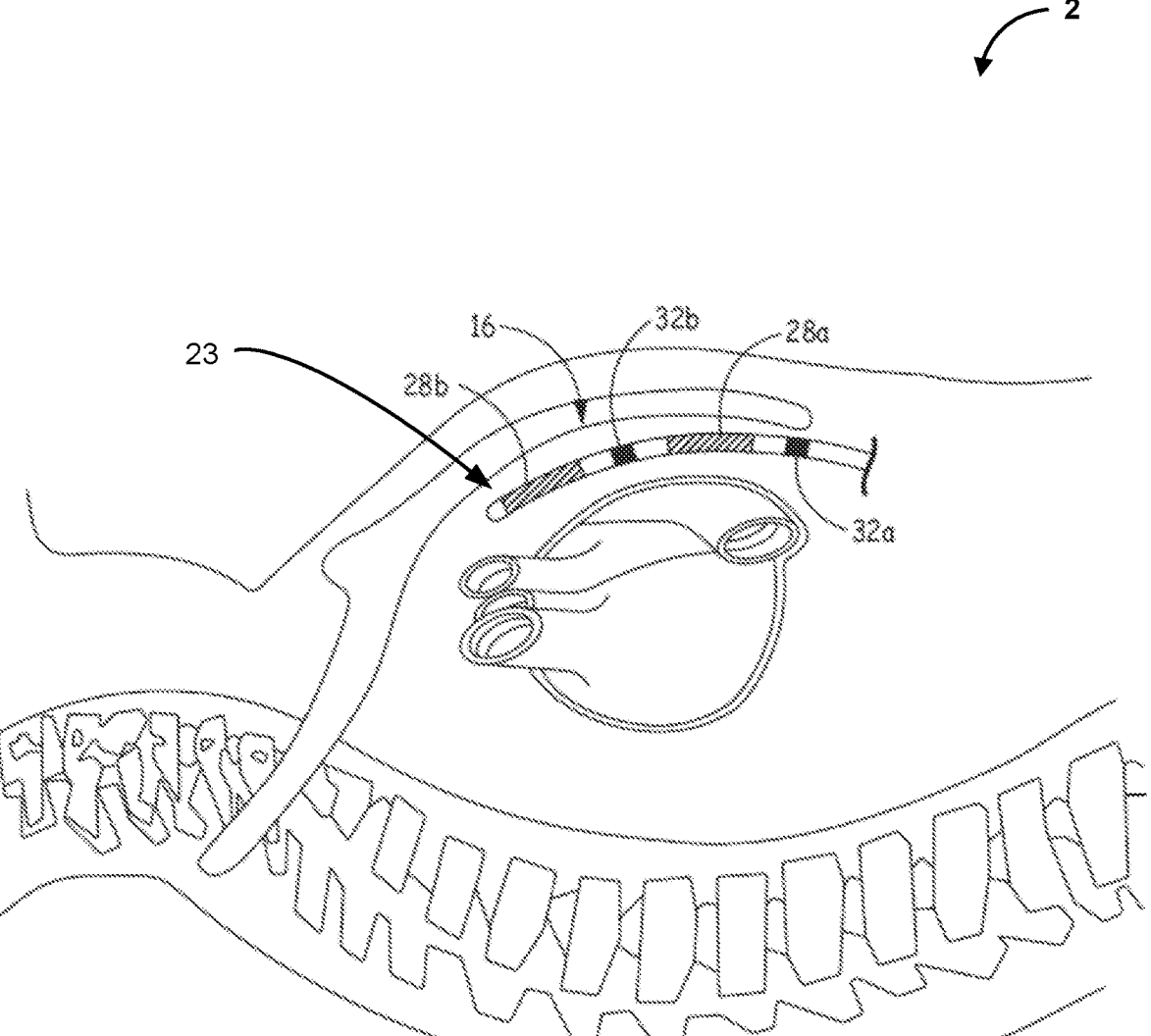
Figure 1C:
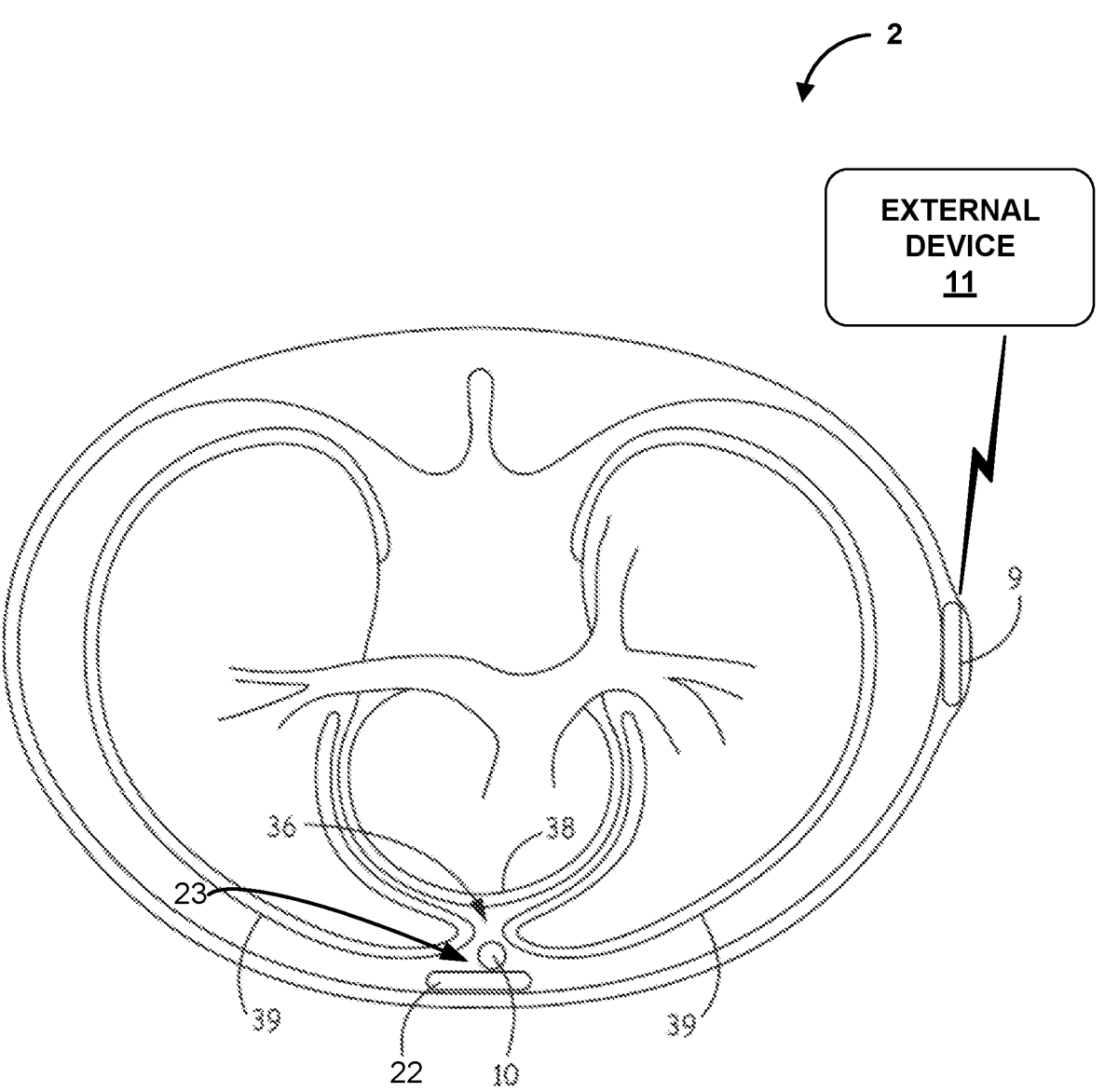

FIGS. 1A-1C are conceptual diagrams illustrating an example medical device system 2 including an implantable cardioverter defibrillator (ICD) system 8, in accordance with one or more techniques of this disclosure. FIG. 1A is a front view of a patient implanted with the ICD system 8. FIG. 1B is a side view of the patient implanted with the ICD system 8. FIG. 1C is a transverse view of the patient implanted with the ICD system 8.

FIG. 1A is a conceptual diagram illustrating a front view of an example medical device system 2, in accordance with one or more techniques of this disclosure. In some examples, medical device system 2 may include an example ICD system 8. ICD system 8 includes an ICD 9 connected to a lead 10. In some examples, ICD 9 may be configured to communicate wirelessly with external device 11.

ICD 9 may include a housing that forms a hermetic seal that protects components of the ICD 9. The housing of ICD 9 may be formed of a conductive material, such as titanium or titanium alloy, which may function as a housing electrode (sometimes referred to as a can electrode). In some embodiments, ICD 9 may be formed to have or may include a plurality of electrodes on the housing. ICD 9 may also include a connector assembly (also referred to as a connector block or header) that includes electrical feedthroughs through which electrical connections are made between conductors of lead 10 and electronic components included within the housing of ICD 9. As will be described in further detail herein, the housing may house one or more processors, memories, transmitters, receivers, sensors, sensing circuitry, therapy circuitry, power sources and other appropriate components. The housing is configured to be implanted in a patient, such patient 12.

ICD 9 may be implanted extra-thoracically on the left side of the patient, e.g., under the skin and outside the ribcage (subcutaneously or submuscularly). ICD 9 may in some instances, be implanted between the left posterior axillary line and the left anterior axillary line of the patient. ICD 9 may however, be implanted at other extra-thoracic locations on the patient as described later.

External device 11 may include a housing which encloses processing circuitry electrically coupled to communication circuitry, acoustic circuitry, a memory, and a user interface. The user interface of external device 11 may include, for example, at least one button. Additionally, or alternatively, the user interface of external device 11 may include any other device, sensor, or medium configured for accepting user input. In some examples, the user interface of external device 11 enables a user to initiate one or more techniques of this disclosure which establish communication with ICD 9 for a period of time. External device 11 is configured to, for example, establish a communication link between external device 11 and ICD 9 by using acoustic signals to activate communication circuitry of ICD 9. In some cases, external device 11 may request information from ICD 9 using acoustic communication. In some cases, external device 11 may instruct ICD 9 to update one or more parameters using acoustic signals.

In some examples, external device 11 may comprise a consumer electronic device such as a tablet, laptop computer, smart phone, or other smart device. External device 11 may be configured to execute an application for controlling and/or programming ICD 9. The application may include one or more user interface screens for display on a touch screen of external device 11. The one or more user interface screens may receive one or more user inputs. In some cases, external device 11 may communicate with ICD 9 in response to receiving one or more user inputs to the user interface screens of the application. In one or more examples where external device 11 is a commercial electronic device, external device 11 may include communication circuitry (e.g., a Bluetooth® radio) configured for communication according to one or more open source communication protocols (e.g., BLE and other Bluetooth® protocols) that are accessible to a wide range of consumer electronic devices. External device 11 may additionally or alternatively include circuitry that is common in consumer electronics such as acoustic emitting circuitry, acoustic receiving circuitry, motion sensors, light sensors, temperature sensors, or any combination thereof.

In some examples, external device 11 is configured for handheld use. In fact, a user may in some cases, be able to fit external device 11 in the palm of a single hand while interacting with the user interface using at least one finger. In addition to being configured for handheld use, external device 11 may be configured to transmit signals via the communication circuitry according to at least one communication protocol and/or transmit signals via the acoustic circuitry according to at least one communication protocol. In some examples, ICD 9 may communicate using one or more open source communication protocols such as Bluetooth® low energy (BLE), other Bluetooth® communication protocols, or other open-source communication protocols.

External device 11 is configured to wirelessly communicate with ICD 9 as needed to provide or retrieve information. In some examples, external device 11 acts as an external programming device, e.g., medical device programmer, for ICD 9. External device 11 is an external computing device that a user, e.g., the clinician and/or patient 12, may use to communicate with ICD 9. For example, external device 11 may be a clinician programmer that the clinician uses to communicate with ICD 9 and update one or more settings of ICD 9. Additionally, or alternatively, external device 11 may be a patient programmer that allows patient 12 to control certain operations of ICD 9 and/or view and modify one or more operational parameter values of ICD 9. The clinician programmer may include more programming features than the patient programmer. In other words, more complex or sensitive tasks may only be allowed by the clinician programmer to prevent an untrained patient from making undesired changes to ICD 9.

External device 11 may be a hand-held computing device with a display viewable by the user and an interface for providing input to external device 11 (i.e., a user input mechanism). For example, external device 11 may include a small display screen (e.g., a liquid crystal display (LCD) or a light emitting diode (LED) display) that presents information to the user. In addition, external device 11 may include a touch screen display, keypad, buttons, a peripheral pointing device, voice activation, or another input mechanism that allows the user to navigate through the user interface of external device 11 and provide input. If external device 11 includes buttons and a keypad, the buttons may be dedicated to performing a certain function, e.g., a power button, the buttons and the keypad may be soft keys that change in function depending upon the section of the user interface currently viewed by the user, or any combination thereof.

In other examples, external device 11 may be a larger workstation or a separate application within another multi-function device, rather than a dedicated computing device. For example, the multi-function device may be a notebook computer, tablet computer, workstation, one or more servers, cellular phone, personal digital assistant, or another computing device that may run an application that enables the computing device to operate as a secure device.

When external device 11 is configured for use by the clinician, external device 11 may be used to transmit instructions to ICD 9. Example instructions may include requests to set electrode combinations for sensing and/or stimulation. The clinician may also configure and store operational parameters for ICD 9 within ICD 9 with the aid of external device 11. In some examples, external device 11 assists the clinician in the configuration of ICD 9 by providing a system for identifying potentially beneficial operational parameter values.

Whether external device 11 is configured for clinician or patient use, external device 11 is configured to communicate with ICD 9 and via wireless communication. External device 11, for example, may communicate according to one or more open source communication protocols such as BLE, other Bluetooth® communication protocols, or other open source communication protocols. ICD 9 and external device 11 may in some cases, use one or more open-source communication protocols as a primary mode of communication. In some examples, external device 11 may send one or more acoustic signals to ICD 9 and/or receive one or more acoustic signals from ICD 9. In some examples, ICD 9 may send one or more acoustic signals to external device 11 and/or receive one or more acoustic signals from external device 11. In some examples, acoustic communication may represent a secondary mode of communication that allows ICD 9 and external device 11 to communicate when a primary mode of communication has failed, is offline, or is disabled for any reason.

In general, ICD 9 and external device 11 may exchange information using at least one communication protocol. Communication protocols define sets of rules that define one or more aspects of data exchange between two or more entities of a network. In some examples, communication protocols are stored as lists of computer-readable instructions and communication protocols may be executed by any combination of hardware (e.g., physical circuitry) and software. An organization, such as a medical device manufacturer, may create its own communication protocols, license communication protocols from a third party, use open-source communication protocols, or perform any combination thereof. In some examples, a communication protocol includes security provisions, such as password requirements and data encryption in order to secure the transfer of data between two or more devices in a network.

ICD 9 collects physiological data from patient 12. ICD 9 may transmit physiological data collected from patient 12 to one or more external devices (e.g., external device 11). Additionally, ICD 9 may receive data indicative of instructions from external device 11, where the instructions cause ICD 9 to, as examples, update one or more settings, change one or more parameters, output data, or delete data.

Since ICD 9 is an implantable device, ICD 9 may be powered using a rechargeable battery or a non-rechargeable battery, or a combination of a non-rechargeable battery and a rechargeable battery). In any case, it may be beneficial to limit an amount of power that ICD 9 consumes from a power source, so that a battery longevity of ICD 9 is extended. Communication circuitry of ICD 9 may consume a significant amount of energy from the power source of ICD 9 such that it is beneficial to transition the communication circuitry of ICD 9 to a reduced power mode, a low-power mode, and/or an offline mode when ICD 9 does not need to use the communication circuitry. But when communication circuitry of ICD 9 is in a reduced power mode, a low-power mode, and/or an offline mode, it might not be possible for external device 11 to communicate with ICD 9 via the communication circuitry. According to one or more techniques described herein, external device 11 may communicate with ICD 9 using one or more communication techniques that do not require communication via the communication circuitry.

In some examples, it may be beneficial for ICD 9 to be smaller in size rather than larger in size. Since ICD 9 is implanted underneath the patient's skin, a smaller ICD may be less noticeable and/or more comfortable for patient 12 as compared with a larger ICD. Since circuitry and other components such as communication circuitry, processing circuitry, stimulation generation circuitry, and memory take space within the ICD 9, it may be beneficial to limit an amount of circuitry and/or other components (e.g., antennae) located within the ICD 9 in order to ensure that the ICD 9 is small in size. Although some ICDs include separate communication circuitry for communicating with external devices while main communication circuitry is powered down or offline, ICD 9 may use acoustic circuitry to communicate with external devices while its communication circuitry is powered down or offline.

ICD 9 may include acoustic receiving circuitry that is configured for sensing one or more physiological signals (e.g., heart sounds) of a heart 26 of patient 12. The acoustic receiving circuitry may additionally or alternatively receive acoustic communication signals from external device 11. This means that ICD 9 may use acoustic receiving circuitry to both sense physiological signals and receive communications, meaning that separate communication is not necessary to communicate with external device 11 while processing circuitry is offline. This may save room within ICD 9 and ensure that ICD 9 is smaller as compared with other ICDs that include separate communication circuitry. The acoustic receiving circuitry is not limited to receiving acoustic communication signals from external devices. In some examples, the acoustic receiving circuitry is configured to receive acoustic voice communications from a human source (e.g., from patient 12 and/or other human sources).

Lead 10 may include an elongated lead body 13 having a distal portion 16 sized to be implanted in an extracardiovascular location proximate the heart, e.g., intra-thoracically, as illustrated in FIGS. 1A-1C, or extra-thoracically. For example, lead 10 may extend extra-thoracically under the skin and outside the ribcage (e.g., subcutaneously or submuscularly) from ICD 9 toward the center of the torso of the patient, for example, toward the xiphoid process 23 of the patient. At a position proximate xiphoid process 23, the lead body 13 may bend or otherwise turn and extend superiorly. The bend may be pre-formed and/or lead body 13 may be flexible to facilitate bending. In the example illustrated in FIGS. 1A-1C, the lead body 13 extends superiorly intra-thoracically underneath the sternum, in a direction substantially parallel to the sternum.

Distal portion 16 of lead 10 may reside in a substernal location such that distal portion 16 of lead 10 extends superior along the posterior side of the sternum substantially within the anterior mediastinum 36. Anterior mediastinum 36 may be viewed as being bounded laterally by pleurae 39, posteriorly by pericardium 38, and anteriorly by the sternum 22. In some instances, the anterior wall of anterior mediastinum 36 may also be formed by the transversus thoracis and one or more costal cartilages. Anterior mediastinum 36 includes a quantity of loose connective tissue (such as areolar tissue), adipose tissue, some lymph vessels, lymph glands, substernal musculature (e.g., transverse thoracic muscle), the thymus gland, branches of the internal thoracic artery, and the internal thoracic vein (ITV).

Lead body 13 may extend superiorly extra-thoracically (instead of intra-thoracically), e.g., either subcutaneously or submuscularly above the ribcage/sternum. Lead 10 may be implanted at other locations, such as over the sternum, offset to the right of the sternum, angled lateral from the proximal or distal end of the sternum, or the like. In some examples, lead 10 may be implanted within an extracardiac vessel within the thorax, such as the ITV, the intercostal veins, the superior epigastric vein, or the azygos, hemiazygos, and accessory hemiazygos veins. In some examples, distal portion 16 of lead 10 may be oriented differently than is illustrated in FIGS. 1A-1C, such as orthogonal or otherwise transverse to sternum 22 and/or inferior to heart 26. In such examples, distal portion 16 of lead 10 may be at least partially within anterior mediastinum 36. In some examples, distal portion 16 of lead 10 may be placed between the heart and lung as well as within the pleural cavity.

Lead body 13 may have a generally tubular or cylindrical shape and may define a diameter of approximately 3-9 French (Fr). However, lead bodies of less than 3 Fr and more than 9 Fr may also be utilized. In another configuration, lead body 13 may have a flat, ribbon, or paddle shape with solid, woven filament, or metal mesh structure, along at least a portion of the length of the lead body 13. In such an example, the width across lead body 13 may be between 1-3.5 mm. Other lead body designs may be used without departing from the scope of this application.

Lead body 13 may be formed from a non-conductive material, including silicone, polyurethane, fluoropolymers, mixtures thereof, and other appropriate materials, and shaped to form one or more lumens (not shown), however, the techniques are not limited to such constructions. Distal portion 16 may be fabricated to be biased in a desired configuration, or alternatively, may be manipulated by the user into the desired configuration. For example, the distal portion 16 may be composed of a malleable material such that the user can manipulate the distal portion into a desired configuration where it remains until manipulated to a different configuration.

Distal portion 16 may include electrodes configured to deliver electrical energy to the heart or sense electrical signals of the heart. Distal portion 16 may be anchored to a desired position within the patient, for example, substernally or subcutaneously by, for example, suturing distal portion 16 to the patient's musculature, tissue, or bone at the xiphoid process entry site. In some examples, distal portion 16 may be anchored to the patient or through the use of rigid tines, prongs, barbs, clips, screws, and/or other projecting elements or flanges, disks, pliant tines, flaps, porous structures such as a mesh-like elements and metallic or non-metallic scaffolds that facilitate tissue growth for engagement, bioadhesive surfaces, and/or any other non-piercing elements.

Lead body 13 may define a substantially linear portion 20 (FIG. 1A) as it curves or bends near the xiphoid process 23 and extends superiorly (e.g., cranially). As shown in FIG. 1A, at least a part of distal portion 16 may define an undulating configuration distal to the substantially linear portion 20. In particular, distal portion 16 may define an undulating pattern, e.g., zigzag, meandering, sinusoidal, serpentine, or other pattern, as it extends toward the distal end of lead 10. In other configurations, lead body 13 may not have a substantially linear portion 20 as it extends superiorly, but instead the undulating configuration may begin immediately after the bend.

Distal portion 16 includes one or more defibrillation electrodes configured to deliver an anti-tachyarrhythmia, e.g., cardioversion/defibrillation, shock to heart 26 of patient 12. In some examples, distal portion 16 includes a plurality of defibrillation electrodes spaced a distance apart from each other along the length of distal portion 16. In the example illustrated by FIGS. 1A-1C, distal portion 16 includes a first defibrillation electrode 28a and a second defibrillation electrode 28b (collectively, "defibrillation electrodes 28").

Defibrillation electrodes 28 may be disposed around or within the lead body 13 of the distal portion 16, or alternatively, may be embedded within the wall of the lead body 13. In one configuration, defibrillation electrodes 28 may be coil electrodes formed by a conductor. The conductor may be formed of one or more conductive polymers, ceramics, metal-polymer composites, semiconductors, metals or metal alloys, including but not limited to, one of a combination of the platinum, tantalum, titanium, niobium, zirconium, ruthenium, indium, gold, palladium, iron, zinc, silver, nickel, aluminum, molybdenum, stainless steel, MP35N, carbon, copper, polyaniline, polypyrrole, and other polymers. In another configuration, each of defibrillation electrodes 28 may be a flat ribbon electrode, a paddle electrode, a braided or woven electrode, a mesh electrode, a directional electrode, a patch electrode or another type of electrode configured to deliver a cardioversion/defibrillation shock to heart 26 of patient 12.

Defibrillation electrodes 28 may be electrically connected to one or more conductors, which may be disposed in the body wall of lead body 13 or in one or more insulated lumens (not shown) defined by lead body 13. In an example configuration, each of defibrillation electrodes 28 is connected to a common conductor such that a voltage may be applied simultaneously to all defibrillation electrodes 28 to deliver an anti-tachyarrhythmia shock to heart 26. In other configurations, defibrillation electrodes 28 may be attached to separate conductors such that each defibrillation electrode 28 may apply a voltage independent of the other defibrillation electrodes 28. In this case, ICD 9 or lead 10 may include one or more switches or other mechanisms to electrically connect the defibrillation electrodes together to function as a common polarity electrode such that a voltage may be applied simultaneously to all defibrillation electrodes 28 in addition to being able to independently apply a voltage.

Distal portion 16 may also include one or more pacing and/or sensing electrodes configured to deliver pacing pulses to heart 26 and/or sense electrical activity of heart 26. Such electrodes may be referred to as pacing electrodes, sensing electrodes, or pace/sense electrodes. In the example illustrated by FIGS. 1A-1C, distal portion 16 includes two pace/sense electrodes 32a and 32b (collectively, "pace/sense electrodes 32").

In the illustrated example of FIGS. 1A-1C, pace/sense electrode 32b is positioned between defibrillation electrodes 28, e.g., within a gap between the defibrillation electrodes, and pace/sense electrode 32a is positioned more proximal along distal portion 16 than proximal defibrillation electrode 28a. In some examples, more than one electrode 32 may exist within the gap between defibrillation electrodes 28. In some examples, an electrode 32 is additionally or alternatively located distal of the distalmost defibrillation electrode 28b.

Electrodes 32 may be configured to deliver low-voltage electrical pulses to the heart or may sense a cardiac electrical activity, e.g., depolarization and repolarization of the heart. As such, electrodes 32 may be referred to herein as pace/sense electrodes 32. In one configuration, electrodes 32 are ring electrodes. However, in other configurations electrodes 32 may be any of a number of different types of electrodes, including ring electrodes, short coil electrodes, paddle electrodes, hemispherical electrodes, or directional electrodes. Each of electrodes 32 may be the same or different types of electrodes as others of electrodes 32. Electrodes 32 may be electrically isolated from an adjacent defibrillation electrode 28 by including an electrically insulating layer of material between electrodes 32 and adjacent defibrillation electrodes 28. Each electrode 32 may have its own separate conductor such that a voltage may be applied to or sensed via each electrode independently from another electrode 32.

Defibrillation electrodes 28 are referred to as defibrillation electrodes, and electrodes 32 are referred to as pace/sense electrodes, because they may have different physical structures enabling different functionality. Defibrillation electrodes 28 may be larger, e.g., have greater surface area, than pace/sense electrodes 32 and, consequently, may be configured to deliver anti-tachyarrhythmia shocks that have relatively higher voltages than pacing pulses. The relatively smaller size of pace/sense electrodes 32 may provide advantages over defibrillation electrodes for delivering pacing pulses and sensing intrinsic cardiac activity, e.g., lower pacing capture thresholds and/or better sensed signal quality. Nevertheless, a defibrillation electrode of defibrillation electrodes 28 may be used to deliver pacing pulses and/or sense electrical activity of the heart, such as in combination with a pace/sense electrode 32.

In the configuration shown in FIGS. 1A-1C, each electrode 32 is substantially aligned along a major longitudinal axis ("x"). In one example, the major longitudinal axis is defined by a portion of lead body 13, e.g., substantially linear portion 20. In another example, the major longitudinal axis is defined relative to the body of the patient, e.g., along the anterior median line (or midsternal line), one of the sternal lines (or lateral sternal lines), left parasternal line, or other line.

In one configuration, the midpoint of each electrode 32a and 32b is along the major longitudinal axis "x," such that each electrode 32a and 32b is at least disposed at substantially the same vertical position when the distal portion is implanted within the patient. In some examples, the longitudinal axis "x" may correspond to a caudal-cranial axis of the patient and a horizontal axis orthogonal to the longitudinal axis "x" may correspond to a medial-lateral axis of the patient. In other configurations, the electrodes 32 may be disposed at any longitudinal or horizontal position along the distal portion 16 disposed between, proximal to, or distal to the defibrillation electrodes 28. In the example illustrated in FIG. 1A, electrodes 32 are disposed along the undulating configuration of distal portion 16 at locations that will be closer to heart 26 of patient 12 than defibrillation electrodes 28 (e.g., at a peak of the undulating configuration that is toward the left side of the sternum). As illustrated in FIG. 1A, for example, electrodes 32 are substantially aligned with one another along the left sternal line. In the example illustrated in FIG. 1A, defibrillation electrodes 28 are disposed along peaks of the undulating configuration that extend toward a right side of the sternum away from the heart. This configuration places pace/sense electrodes 32 at locations closer to the heart than defibrillation electrodes 28, to facilitate cardiac pacing and sensing at relatively lower amplitudes.

In some examples, pace/sense electrodes 32 and the defibrillation electrodes 28 may be disposed in a common plane when distal portion 16 is implanted extracardiovascularly. In other configurations, the undulating configuration may not be substantially disposed in a common plane. For example, distal portion 16 may define a concavity or a curvature.

Proximal end 14 of lead body 13 may include one or more connectors 34 to electrically couple lead 10 to ICD 9. ICD 9 may also include a connector assembly that includes electrical feedthroughs through which electrical connections are made between the one or more connectors 34 of lead 10 and the electronic components included within the housing. The housing of ICD 9 may house one or more processors, memories, transmitters, receivers, sensors, sensing circuitry, therapy circuitry, power sources (e.g., capacitors and batteries), and/or other components. The components of ICD 9 may generate and deliver electrical therapy such as anti-tachycardia pacing, cardioversion or defibrillation shocks, post-shock pacing, and/or bradycardia pacing.

The undulating configuration of distal portion 16 and the inclusion of electrodes 32 between defibrillation electrodes 28 may provide a number of therapy vectors for the delivery of electrical therapy to the heart. For example, at least a portion of defibrillation electrodes 28 and one of electrodes 32 may be disposed over the right ventricle, or any chamber of the heart, such that pacing pulses and anti-tachyarrhythmia shocks may be delivered to the heart. The housing of ICD 9 may be charged with or function as a polarity different than the polarity of the one or more defibrillation electrodes 28 and/or electrodes 32 such that electrical energy may be delivered between the housing and the defibrillation electrodes 28 and/or electrodes 32 to the heart.

Each defibrillation electrode of defibrillation electrodes 28 may have the same polarity as every other defibrillation electrode of defibrillation electrodes 28 when a voltage is applied to it such that a shock may be delivered from all defibrillation electrodes together. In examples in which defibrillation electrodes 28 are electrically connected to a common conductor within lead body 13, this is the only configuration of defibrillation electrodes 28. However, in other examples, defibrillation electrodes 28 may be coupled to separate conductors within lead body 13 and may therefore each have different polarities such that electrical energy may flow between defibrillation electrodes 28, or between one of defibrillation electrodes 28 and one of pace/sense electrodes 32 or the housing electrode, to provide anti-tachyarrhythmia shock, pacing therapy, and/or to sense cardiac depolarizations. In this case, defibrillation electrodes 28 may still be electrically coupled together, e.g., via one or more switches within ICD 9, to have the same polarity.

In some examples, distal portion 16 of lead 10 may include one or more shields. The shield or shields may be configured to impede an electric field from delivery of an electrical therapy via an electrode, e.g., from a pacing pulse, in a direction from the electrode away from the heart, e.g., in an anterior direction. In this manner, the shield may reduce the likelihood that the electrical field will stimulate extracardiac tissue, such as sensory or motor nerves. Furthermore, the shield may direct the electrical field toward the heart, allowing lower energy level pacing pulses to capture the heart than may be required without the shield. Lower energy pacing pulses may also reduce the likelihood that pacing pulses delivered via the pacing electrode stimulate extracardiac tissue and may result in less consumption of the power source of ICD 9 and, consequently, longer service life for the ICD. The techniques of this disclosure may be applied to implantable systems other than ICD 9, including, but not limited to, bradycardia pacemaker systems. For example, a lead that does not include defibrillation electrodes may include one or more shields and may be used with a pacemaker system without defibrillation capabilities.

In accordance with the techniques of the disclosure, the pacing electrode of pace/sense electrodes 32 may be configured to decrease the pacing voltage threshold. For example, a conductive surface may be disposed on a shield and electrically coupled to the pacing electrode, which may reduce a resistance of the pacing electrode and/or expand an electric field generated by the pacing electrode. Reducing the resistance of the pacing electrode and/or expanding the electric field generated by the pacing electrode may reduce an amount of current used to generate a pacing pulse, which may decrease an amount of power used by ICD 9.

For example, lead 10 may include first defibrillation electrode 28a and second defibrillation electrode 28b that are configured to deliver anti tachyarrhythmia shocks. In this example, pacing electrode 32b may be configured to deliver a pacing pulse that generates an electric field proximate to the pacing electrode. A shield may be disposed over at least a portion of an outer surface of pacing electrode 32b and extending laterally away from the pacing electrode 32b. The shield may be configured to impede the electric field in a direction from pacing electrode 32b away from the heart. In some examples, the shield may be disposed between first defibrillation electrode 28a and second defibrillation electrode 28b. A conductive surface may be disposed on the shield and electrically coupled to pacing electrode 32b. Further details of the shield and conductive surface are discussed with respect to FIGS. 3A, 3B.

ICD 9 includes acoustic receiving circuitry configured to receive one or more acoustic signals. Acoustic signals may include one or more acoustic communication signals and/or one or more acoustic biometric signals. That is, the acoustic receiving circuitry of ICD 9 may be configured to sense one or more biometric signals that are indicative of physiological functions of the patient. For example, acoustic receiving circuitry may sense one or more heart sounds of the heart 26 of patient 12. ICD 9 may track one or more patient conditions based on heart sounds received via the acoustic receiving circuitry. For example, the heart sounds may indicate whether a heart failure condition of patient 12 is worsening. ICD 9 may in some examples, deliver therapy based on acoustic biometric signals received via the acoustic receiving circuitry.

Additionally, or alternatively, acoustic receiving circuitry of ICD 9 may be configured to receive one or more acoustic communication signals via the acoustic receiving circuitry. Acoustic communication signals may be sent from another device (e.g., external device 11) to ICD 9, whereas acoustic biometric signals may represent sounds caused by physiological functions of patient 12. In some examples, ICD 9 may receive a sequence of acoustic communication signals from external device 11 that are separate from acoustic biometric signals corresponding to physiological functions of patient 12. ICD 9 may be configured to determine that the acoustic communication signals represent communications and not physiological signals. ICD 9 may be configured to determine that the acoustic biometric signals represent biometric signals and not communication signals. In this way, acoustic receiving circuitry of ICD 9 may be configured to both collect patient data and communicate with other devices using acoustic signals. Acoustic receiving circuitry of ICD 9 may thus perform two functions that are useful to the operation of ICD 9.

Processing circuitry of ICD 9 may receive, via acoustic receiving circuitry of ICD 9 from external device 11, a sequence of acoustic communication signals that are separate from the one or more acoustic biometric signals. The processing circuitry of ICD 9 may decode the sequence of acoustic communication signals to identify one or more requested actions. The processing circuitry of ICD 9 may control the ICD to perform the one or more requested actions. ICD 9 decoding a sequence of acoustic communication signals may include recognizing the one or more requested actions in the sequence of acoustic communication signals.

In some examples, the one or more requested actions may include a request to establish a communication link between ICD 9 and external device 11. The communication link may represent a communication link via communication circuitry of ICD 9 and according to a communication protocol (e.g., a Bluetooth® communication protocol). In some examples, communication according to the BLE protocol via the communication circuitry of ICD 9 represents a primary method of communication for ICD 9. ICD 9 may receive the sequence of acoustic communication signals from external device 11 when the communication circuitry of ICD 9 occupies a low-power mode or an offline mode such that communication circuitry of ICD 9 does not consume a large amount of power and cannot communicate according to the communication protocol. In some examples, ICD 9 may transition the communication circuitry of ICD 9 from operating at a low-power mode to operating at a high-power mode to enable communication according to the communication protocol in response to receiving the sequence of acoustic communication signals from external device 11 via the acoustic receiving circuitry of ICD 9. In other words, the ICD 9 may transition the communication circuitry to a mode that consumes a greater amount of power in response to receiving acoustic communication from an external device indicating a request to communicate according to the communication protocol. ICD 9 may establish the communication link between the ICD 9 and the external device 11 in response to transitioning the communication circuitry from the low-power mode to the high-power mode.

The processing circuitry of ICD 9 may be configured to receive, via the communication link between ICD 9 and the external device 11, a request to terminate the communication link. The processing circuitry of ICD 9 may transition the communication circuitry from operating at the high-power mode to operating at the low-power mode based on receiving the request to terminate the communication link. That is, the processing circuitry of ICD 9 may transition the communication circuitry from operating at the high-power mode to operating at the low-power mode when the communication link is no longer necessary, thus preserving a power level of the power source of ICD 9. It may be beneficial only to use the communication circuitry when necessary for communication needs in order to extend a longevity of ICD 9.

ICD 9 may in some examples, include acoustic transmission circuitry configured to generate one or more acoustic signals for output that are separate from acoustic signals that are received via acoustic receiving circuitry of ICD 9. For example, ICD 9 may be configured to determine that a first sequence of acoustic communication signals received by acoustic receiving circuitry of ICD 9 comprises a request to provide status information corresponding to the ICD 9. Processing circuitry of ICD 9 may be configured to control the acoustic transmission circuitry of ICD 9 to generate a second sequence of acoustic communication signals for output to the external device 11, wherein the second sequence of acoustic communication signals comprises the status information corresponding to the ICD 9. That is, ICD 9 may be configured to provide status information without using communication circuitry, thus preserving a power level of a power source of ICD 9. In some examples, it may consume a smaller amount of power to transmit the status information via acoustic signals as compared with transmitting the status information via the communication circuitry of ICD 9.

In some examples, to decode the sequence of acoustic communication signals received by ICD 9 via the acoustic reception circuitry, the processing circuitry of ICD 9 is further configured to determine that the sequence of acoustic communication signals comprises a request to update one or more parameters of the ICD 9. The processing circuitry of ICD 9 is further configured to update, based on the request to update one or more parameters of ICD 9, the one or more parameters of ICD 9. In some examples, the request to update the one or more parameters of the ICD 9 comprises a request to implement a therapy mode, and the processing circuitry of ICD 9 is configured to implement the therapy mode based on the request to implement the therapy mode.

ICDs and other implantable medical devices may be capable of recording an acoustic signal of the heart (e.g., a signal indicating one or more "heart sounds") while implanted. Processing circuitry may evaluate the acoustic signal to determine a variety of different characteristics of cardiac function, including worsening heart failure, among many other potential applications disclosed by others. In some examples, ICD 9 may include a piezoelectric element configured to capture the acoustic signal including the heart sounds. In some examples, the piezoelectric element may additionally or alternatively be used for audible patient alert signaling.

ICD 9 may in some examples, use BLE as a primary mode of communication with other devices (e.g., external device 11). In some cases, an IMD may use a secondary mode of communication or a backup mode of communication when the primary mode of communication fails or is offline. Some ICDs and other IMDs use proprietary communication protocols and separate communication circuitry for a secondary mode of communication. Separate communication circuitry for executing one or more secondary communication protocols occupies space within the IMD, and IMDs that do not have separate communication circuitry for executing secondary communication protocols may be smaller than IMDs that include separate communication circuitry for executing secondary communication protocols. It may be beneficial for IMDs to be smaller as opposed to larger, because a larger IMD implanted underneath the patient's skin may cause a greater amount of discomfort, require more invasive implant procedures, and have a shorter battery longevity as compared with smaller IMDs.

Proprietary communication protocols may in some cases, require specialized external programmers and remote monitoring instruments for execution. These specialized instruments may be unwieldy and expensive to maintain. It may be beneficial for an external programmer to comprise a consumer electronic device (e.g., a tablet, a laptop computer, or a mobile phone) executing an application, and it may be difficult for a consumer electronic device executing an application to implement a proprietary communication protocol. In some examples, proprietary communication protocols are less secure than open source communication protocols such as BLE. In some examples, ICD 9 and external device 11 may implement one or more techniques for acoustic signaling as a secondary mode of communication instead of using proprietary communication protocols which require ICD 9 to include communication circuitry in addition to the circuitry for implementing one or more primary communication protocols.

In some examples, external device 11 may be configured to emit one or more custom sounds. External device 11 may in some cases, comprise a consumer electronic device such as a smartphone or tablet that includes circuitry for generating one or more acoustic signals and circuitry for receiving one or more acoustic signals. External device 11 may emit one or more custom sounds that could be detected by ICD 9 to illicit an action or response. In some examples, sounds emitted by external device 11 are audible to humans, but this is not necessary. In some examples, sounds emitted by external device 11 are inaudible to humans. In any case, ICD 9 may be configured to detect the one or more acoustic signals emitted by external device 11. Acoustic signals emitted by external device 11 may in some cases, be encoded with signaling information so that the acoustic signals include messages and/or security codes for ICD 9.

Acoustic signals emitted by ICD 9 may initiate a programmer session request. For example, in response to a user interface of external device 11 receiving a user input to a "start session" button, external device 11 may output one or more acoustic signals including a request to establish a communication link. In response to receiving the one or more acoustic signals, ICD 9 may activate communication circuitry for communicating according to a primary communication protocol (e.g., BLE). For example, ICD 9 may activate a Bluetooth® radio. In some examples, activating the communication circuitry may involve transitioning the processing circuitry from a low power state to a high power state. In some examples, activating the communication circuitry may involve transitioning the processing circuitry from a no-power state that does not draw any power from the power source of ICD 9 to a powered-up state that draws power from the power source of ICD 9.

In some examples, activating the communication circuitry may involve transitioning the processing circuitry from a low power state where the communication circuitry emits advertising signals at a low advertising rate to a high power state where the communication circuitry emits advertising signals at a high advertising rate that is greater than the low advertising rate. For example, when communication circuitry of ICD 9 is in a low power mode, ICD 9 may output advertising signals via the communication circuitry at a low interval rate (e.g., every minute, every three minutes, every five minutes). These advertising signals may indicate that ICD 9 is available to establish a communication link. The low interval rate may in some examples, represent a rate that does not cause communication circuitry to draw a large amount of power from the power source of ICD 9 so that a battery longevity of ICD 9 is extended. In some examples, ICD 9 may transition the communication circuitry from a low advertising rate to a high advertising rate that is greater than the low advertising rate (e.g., every 500 milliseconds (ms), every second, every two seconds).

A high advertising rate may enable ICD 9 to establish a communication link with external device 11 via the communication protocol. In some examples, ICD 9 may transition the communication circuitry from a low advertising rate to the high advertising rate in response to receiving one or more acoustic signals. By transitioning the communication circuitry from the low advertising rate to the high advertising rate in response to receiving one or more acoustic signals via acoustic receiving circuitry that is also configured to sense acoustic biometric signals, ICD 9 may transition the communication circuitry from the low advertising rate to the high advertising rate without including separate communication circuitry and/or components for receiving signals to transition the communication circuitry to the high advertising rate. In other words, ICD 9 may conserve power when the communication circuitry is operating in the low power mode and emitting advertisements at the low advertising rate, and ICD 9 may transition the communication circuitry from the low power mode to the high power mode in response to receiving one or more acoustic communication signals via acoustic receiving circuitry that is also configured to sense acoustic biometric signals. This may allow ICD 9 to receive communication signals to transition the communication circuitry from the low power mode to the high power mode via circuitry that is present within ICD 9 for another purpose (e.g., sensing biometric signals) without including separate communication circuitry for receiving communication signals to transition the communication circuitry from the low power mode to the high power mode.

In some examples, external device 11 and ICD 9 may use acoustic communication instead of regular advertising according to a primary communication protocol such as BLE. Some IMDs may exchange advertising signals over BLE according to time intervals (e.g., every 30 seconds, every minute, every three minutes, or any other interval of time). ICD 9 may in some examples, emit one or more acoustic advertising signals via acoustic transmission circuitry instead of emitting one or more advertising signals via the communication circuitry. For example, ICD 9 may control acoustic transmission circuitry to emit acoustic advertising signals at a low advertising rate without emitting advertising signals via communication circuitry, thus allowing the communication circuitry to be substantially powered down. In some examples, ICD 9 may transition the communication circuitry from a substantially powered down mode to a high power mode in response to receiving one or more acoustic communication signals via acoustic receiving circuitry. ICD 9 may in some cases, receive one or more acoustic signals from external device 11 instead of receiving one or more advertising signals from external device 11 according to a primary communication protocol such as BLE.

When a primary mode of communication such as BLE fails or goes offline, ICD 9 may send and/or receive one or more acoustic signals as a secondary mode of communication. For example, external device 11 may send acoustic signals to check a status byte of ICD 9. In response to receiving one or more acoustic signals to check status byte, external device 11 may respond by generating one or more acoustic signals including contents of an alert status byte corresponding to ICD 9.

In some examples, ICD 9 may deliver therapy according to one or more therapy modes. It may be necessary in some cases to set a therapy mode in the case of an emergency or when a primary mode of communication between external device 11 and ICD 9 is offline. For example, external device 11 may instruct ICD 9 to an emergency mode with prespecified values for pacing, detection and arrythmia therapy device parameters. In the event of a failure of a primary mode of communication such as BLE, external device 11 may send programming instructions to ICD 9 via acoustic communication.

In some examples, ICD 9 may send security codes or other controls to mitigate security risks via acoustic signaling. For example, to establish a communication link via communication circuitry of ICD 9 according to a primary communication protocol (e.g., BLE), ICD 9 and external device 11 may exchange one or more encryption keys to secure the communication link between ICD 9 and external device 11. In some examples, it may be beneficial to exchange encryption keys via a secure mode of communication other than the primary communication protocol until the secure communication link according to the primary communication protocol is fully established. ICD 9 may in some examples, send one or more encryption keys to external device 11 via acoustic transmission circuitry and/or receive one or more encryption keys from external device 11 via acoustic receiving circuitry. This may allow ICD 9 to securely exchange encryption keys via acoustic communication to establish a secure communication link with external device 11 according to the primary communication protocol without including separate communication circuitry for securely exchanging encryption keys.

FIG. 1B is a conceptual diagram illustrating a side view of an example medical device system 2, in accordance with one or more techniques of this disclosure. For example, the side view illustrated in FIG. 1B illustrates a distal portion 16 of the lead body 13 of lead 10. As seen in FIG. 1B, the distal portion 16 of the lead body 13 is located within the xiphoid process 23 of the patient 12.

FIG. 1C is a conceptual diagram illustrating a transverse view of an example medical device system 2, in accordance with one or more techniques of this disclosure. As seen in FIG. 1C, ICD 9 is implanted under the patient's skin on a side of the patient and lead 10 is implanted within the xiphoid process 23 underneath the sternum 22.

Although the medical device system 2 of FIGS. 1A-1C illustrate an ICD system 8 including an ICD 9, other example medical device systems may include IMDs other than ICDs such as pacemakers, cardiac resynchronization therapy devices (CRT-Ds), insertable cardiac monitors (ICMs), spinal cord stimulation (SCS) devices, deep brain stimulation (DBS) devices, left ventricular assist devices (LVADs), implantable sensors, orthopedic devices, drug pumps, or any combination thereof. Techniques of this disclosure may be used for acoustic communication with any one of the aforementioned IMDs. Moreover, techniques described in this disclosure may be applied to facilitate communication between two or more devices, where none of the two or more devices are implantable devices. Additionally, in some examples, techniques described in this disclosure may be applied to facilitate acoustic communication between two or more devices, where none of the two or more devices are medical devices.

Figure 2:
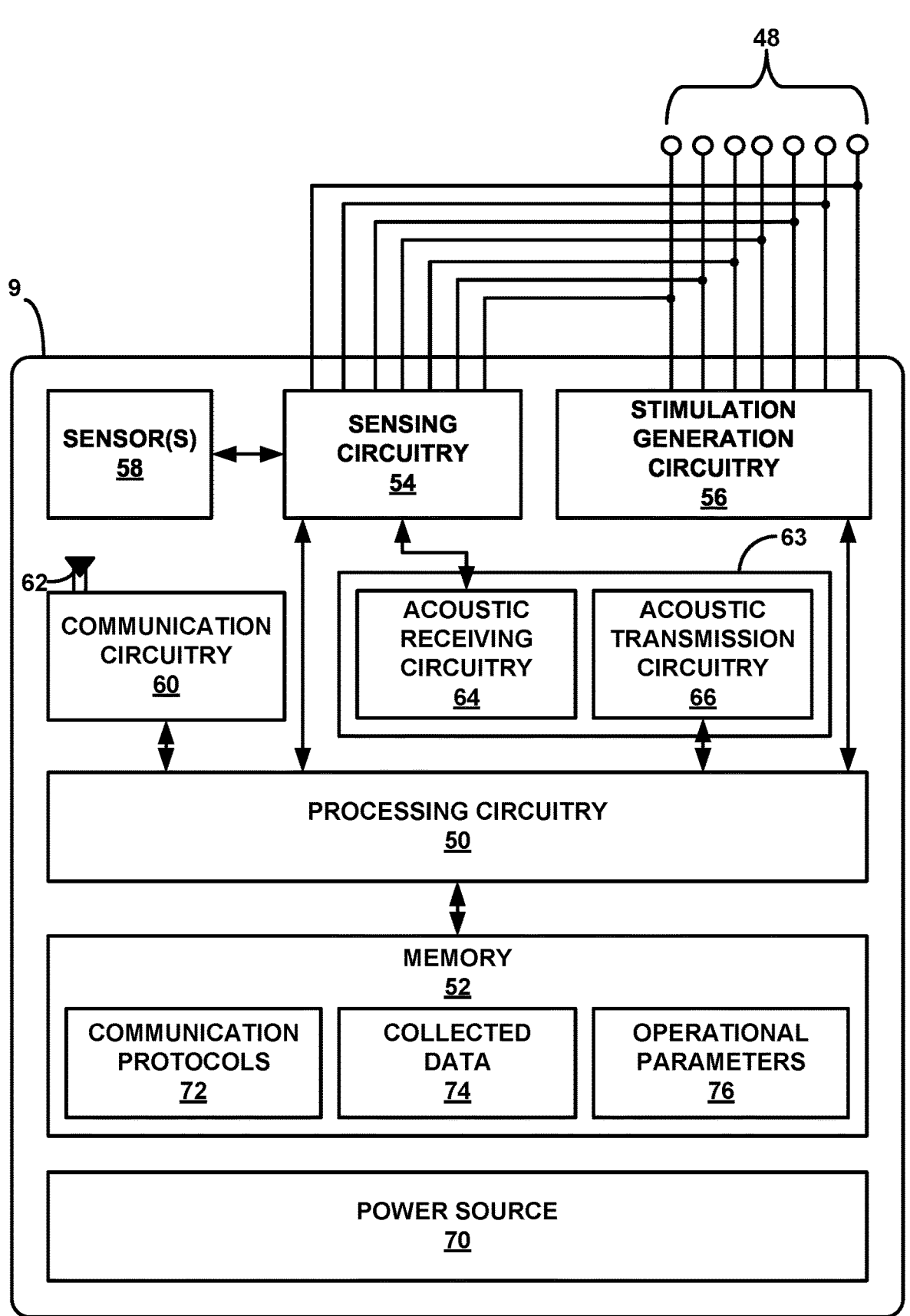
FIG. 2 is a block diagram illustrating an example configuration of components of an ICD system, in accordance with one or more techniques of this disclosure.

FIG. 2 is a block diagram illustrating an example configuration of components of ICD system 8, in accordance with one or more techniques of this disclosure. In the example of FIG. 2, ICD system 8 includes ICD 9 and electrodes 48. ICD system 8 may include one or more leads that include one or more of electrodes 48. ICD 9 includes processing circuitry 50, memory 52, sensing circuitry 54, stimulation generation circuitry 56, sensor(s) 58, communication circuitry 60, antenna 62, acoustic circuitry 63 including acoustic receiving circuitry 64 and/or acoustic transmission circuitry 66, and power source 70, memory 52 is configured to store communication protocols 72, collected data 74, and operational parameters 76. In some examples, electrodes 48 may include defibrillation electrodes 28, pace/sense electrodes 32, one or more other electrodes, or any combination thereof.

Processing circuitry 50, in one example, may include one or more processors that are configured to implement functionality and/or process instructions for execution within ICD 9. For example, processing circuitry 50 may be capable of processing instructions stored in memory 52. Processing circuitry 50 may include, for example, microprocessors, digital signal processors (DSPs), application specific integrated circuits (ASICs), field-programmable gate arrays (FPGAs), or equivalent discrete or integrated logic circuitry, or a combination of any of the foregoing devices or circuitry. Accordingly, processing circuitry 50 may include any suitable structure, whether in hardware, software, firmware, or any combination thereof, to perform the functions ascribed herein to processing circuitry 50.

Memory 52 may be configured to store information within ICD 9 during operation. Memory 52 may include a computer-readable storage medium or computer-readable storage device. In some examples, memory 52 includes one or more of a short-term memory or a long-term memory. Memory 52 may include, for example, random access memories (RAM), dynamic random-access memories (DRAM), static random-access memories (SRAM), magnetic discs, optical discs, flash memories, or forms of electrically programmable memories (EPROM) or electrically erasable and programmable memories (EEPROM). In some examples, memory 52 is used to store data indicative of instructions for execution by processing circuitry 50.

Sensing circuitry 54 monitors electrical cardiac signals from any combination of electrodes 48. In some examples, sensing circuitry 54 may include one or more amplifiers, filters, and analog-to-digital converters. For example, sensing circuitry 54 may include one or more detection channels, each of which may include an amplifier. The detection channels may be used to sense cardiac signals, such as a cardiac EGM. Some detection channels may detect events, such as R-waves, P-waves, and T-waves and provide indications of the occurrences of such events to processing circuitry 50. Additionally, or alternatively, some channels may detect cardiac EGM signals from a particular combination of electrodes 48. One or more other detection channels may provide signals to an analog-to-digital converter, for conversion into a digital signal for processing, analysis, storage, or output by processing circuitry 50.

Sensing circuitry 54 may be electrically coupled to some or all of electrodes 48, which may correspond to any of the defibrillation, pace/sense, and housing electrodes described herein. Sensing circuitry 54 is configured to obtain signals sensed via one or more combinations of electrodes 48 and process the obtained signals.

The components of sensing circuitry 54 may be analog components, digital components, or a combination thereof. Sensing circuitry 54 may for example, include one or more sense amplifiers, filters, rectifiers, threshold detectors, analog-to-digital converters (ADCs) or the like. Sensing circuitry 54 may convert the sensed signals to digital form and provide the digital signals to processing circuitry 50 for processing or analysis. For example, sensing circuitry 54 may amplify signals from the sensing electrodes and convert the amplified signals to multi-bit digital signals by an ADC. Sensing circuitry 54 may also compare processed signals to a threshold to detect the existence of atrial or ventricular depolarizations (e.g., P waves or R waves) and indicate the existence of the atrial depolarization (e.g., P waves) or ventricular depolarizations (e.g., R-waves) to processing circuitry 50.

Processing circuitry 50 may process the signals from sensing circuitry 54 to monitor electrical activity of heart 26 of patient 12. Processing circuitry 50 may store signals obtained by sensing circuitry 54 as well as any generated EGM waveforms, marker channel data or other data derived based on the sensed signals in memory 52. Processing circuitry 50 may analyze the EGM waveforms and/or marker channel data to detect arrhythmias (e.g., bradycardia or tachycardia). In response to detecting the cardiac event, processing circuitry 50 may control stimulation generation circuitry 56 to deliver the desired therapy to treat the cardiac event, e.g., defibrillation shock, cardioversion shock, ATP, post shock pacing, or bradycardia pacing.

Stimulation generation circuitry 56 is configured to generate and deliver electrical therapy to heart 26. Stimulation generation circuitry 56 may include one or more pulse generators, capacitors, and/or other components capable of generating and/or storing energy to deliver as pacing therapy, defibrillation therapy, cardioversion therapy, cardiac resynchronization therapy, other therapy, or a combination of therapies. In some instances, stimulation generation circuitry 56 may include a first set of components configured to provide pacing therapy and a second set of components configured to provide defibrillation therapy. In some instances, stimulation generation circuitry 56 may utilize the same set of components to provide both pacing and defibrillation therapy. In still other instances, stimulation generation circuitry 56 may share some of the defibrillation and pacing therapy components while using other components solely for defibrillation or pacing. Processing circuitry 50 may control stimulation generation circuitry 56 to deliver the generated therapy to heart 26 via one or more combinations of electrodes 48. Although not shown in FIG. 2, ICD 9 may include switching circuitry configurable by processing circuitry 50 to control which of electrodes 48 is connected to sensing circuitry 54 and stimulation generation circuitry 56.

As shown in FIG. 2, ICD 9 may include sensor(s) 58, such as one or more accelerometers, which may be configured to provide signals indicative of other parameters of a patient, such as activity, posture, or temperature to processing circuitry 50 via sensing circuitry 54. In some examples, sensing circuitry 54 is electrically coupled to sensor(s) 58. Sensor(s) 58 may include any combination of accelerometers, temperature sensors, chemical sensors, light sensors, pressure sensors, or other kinds of sensor. Sensor(s) 58 may for example, sense one or more physiological parameters indicative of a heart condition. Additionally, or alternatively, an accelerometer of sensor(s) 58 may sense data indicative of at least one of patient posture and patient activity.

Communication circuitry 60 may include any suitable hardware, firmware, software, or any combination thereof for communicating with another device, such as external device 11. For example, communication circuitry 60 may include appropriate modulation, demodulation, frequency conversion, filtering, and amplifier components for transmission and reception of data. Under the control of processing circuitry 50, communication circuitry 60 may receive downlink telemetry from, as well as send uplink telemetry to external device 11 or another device with the aid of an internal or external antenna, e.g., antenna 62. Communication circuitry 60 may include any combination of a Bluetooth® radio, an electronic oscillator, frequency modulation circuitry, frequency demodulation circuitry, amplifier circuitry, and power switches such as a metal-oxide-semiconductor field-effect transistors (MOSFET), a bipolar junction transistor (BJT), an insulated-gate bipolar transistor (IGBT), a junction field effect transistor (JFET), or another element that uses voltage for its control.

Acoustic circuitry 63 may include acoustic receiving circuitry 64 and acoustic transmission circuitry 66. Acoustic receiving circuitry 64 may include one or more acoustic sensors configured to generate one or more electrical signals for output to sensing circuitry 54 based on receiving one or more acoustic signals. For example, acoustic sensors of acoustic receiving circuitry 64 receive one or more acoustic signals, the acoustic sensors may generate an electrical signal that indicates one or more parameters of the received acoustic signals. For example, the electrical signal generated by the acoustic sensors may indicate a magnitude of one or more received acoustic signals, a duration of one or more received acoustic signals, a frequency of one or more received acoustic signals, or any combination thereof. In some examples, acoustic receiving circuitry 64 may include one or more piezoelectric transducers configured to generate an electrical signal in response to receiving acoustic signals.

In some examples, acoustic receiving circuitry 64 may be configured to sense one or more acoustic biometric signals. For example, acoustic receiving circuitry 64 may be configured to sense heart sounds emitted by the heart 26 of patient 12 or one or more other kinds of acoustic biometric signals caused by physiological functions of patient 12.

Acoustic receiving circuitry 64 may be configured to generate one or more electrical signals that indicate the one or more acoustic biometric signals sensed by acoustic receiving circuitry 64. Processing circuitry 50 may process the one or more electrical signals generated by acoustic receiving circuitry 64 in order to monitor one or more patient conditions, determine one or more physiological parameter values, determine one or more therapy parameters, or any combination thereof.

Heart sounds are made by the heart 26 during the course of the cardiac cycle. For example, the first heart sound (S1) is a sound that occurs when the mitral and tricuspid valves of the heart 26 close. The mitral and tricuspid valves are the valves that separate the atria and the ventricles of the heart. This means that the first heart sound (S1) caused by the closure of the mitral and tricuspid valves indicates a point in the cardiac cycle, such that ICD 9 may track the first heart sound (S1) over time to determine one or more cardiac parameters (e.g., heart rate, heart rate variability) of the patient 12. The second heart sound (S2) is caused by the closure of the aortic and pulmonary valves of the heart 26. Blood passes through the aortic and pulmonary valves of the heart 26 as it leaves the ventricles of the heart 26, so the closure of the aortic and pulmonary valves of the heart 26 as indicated by the second heart sound (S2) are important events in the cardiac cycle. The third heart sound (S3) is caused by a transition from rapid to slow filling of the ventricle during the early diastole. The fourth heart sound (S4) may be caused by atrial contraction in the late diastole. One or more electrical signals generated by acoustic receiving circuitry 64 in response to receiving acoustic signals may indicate S1, S2, S3, S4, or any combination thereof. One or more electrical signals generated by acoustic receiving circuitry 64 in response to receiving acoustic signals may indicate one or more other acoustic biometric signals.

In some examples, acoustic receiving circuitry 64 may be configured to sense one or more acoustic communication signals. The one or more acoustic communication signals may represent acoustic communication signals emitted by another device to communicate with ICD 9. For example, external device 11 or another device may emit one or more acoustic communication signals and acoustic receiving circuitry 64 may sense the one or more acoustic communication signals. One or more acoustic sensors of acoustic receiving circuitry 64 may generate one or more electrical signals that indicate the one or more acoustic communication signals. In some examples, the one or more acoustic communication signals may represent acoustic communication signals from a human source.

Acoustic receiving circuitry 64 may in some examples, receive a sequence of acoustic communication signals. In some examples, the sequence of acoustic communication signals may include one or more instructions or requests. For example, a sequence of acoustic communication signals may include a request to establish a communication link, provide information, or update one or more parameters of ICD 9. Processing circuitry 50 may decode the sequence of acoustic communication signals in order to identify the one or more instructions or requests.

In some examples, processing circuitry 50 may be configured to process a signal received from acoustic receiving circuitry 64 via sensing circuitry 54 and identify one or more acoustic biometric signals and/or one or more acoustic communication signals. In some examples, processing circuitry 50 may be configured to identify acoustic biometric signals as being separate from one or more acoustic communication signals. This means that even when acoustic receiving circuitry 64 senses both acoustic biometric signals and acoustic communication signals at substantially the same time, processing circuitry 50 may be configured to identify both of the acoustic biometric signals and the acoustic communication signals as being separate from each other.

Acoustic circuitry 63 may include acoustic transmission circuitry 66. In some examples, acoustic transmission circuitry 66 may be configured to generate one or more acoustic signals for output from ICD 9. For example, acoustic transmission circuitry 66 may include one or more piezoelectric transducers or one or more other components configured to generate acoustic signals. Processing circuitry 50 may be configured to control acoustic transmission circuitry 66 to generate one or more acoustic signals for output that are separate from one or more acoustic transmission circuitry received by acoustic receiving circuitry 64 from external device 11. In some examples, processing circuitry 50 may control acoustic transmission circuitry 66 to generate acoustic signals that include information. In some examples, acoustic receiving circuitry 64 and acoustic transmission circuitry 66 may share circuitry and/or one or more other components. For example, a piezoelectric transducer may be configured to both sense audio signals and generate audio signals. In some examples not illustrated in FIG. 2, acoustic circuitry 63 may include acoustic receiving circuitry 64 without including any acoustic transmission circuitry.

Power source 70 is configured to deliver operating power to the components of ICD 9. Power source 70 may include a battery and a power generation circuit to produce the operating power. In some examples, the battery is rechargeable to allow extended operation. In some examples, recharging is accomplished through proximal inductive interaction between an external charger and an inductive charging coil within external device 11. It is not required for power source 70 to be rechargeable. In some examples, power source 70 is not rechargeable, and ICD 9 is designed to operate on a single charge of power source 70. Power source 70 may include any one or more of a plurality of different battery types, such as nickel cadmium batteries and lithium-ion batteries.

Memory 52 may be configured to store communication protocols 72. In some examples, communication protocols 72 may include one or more Bluetooth® communication protocols (e.g., BLE and/or other Bluetooth® communication protocols) for sending and receiving communications via a Bluetooth® radio of communication circuitry 60. In some examples, communication protocols 72 may include one or more communication protocols other than Bluetooth® communication protocols for sending and receiving communications via communication circuitry 60. Communication protocols may include one or more rules, standards, or parameters for communicating with one or more other devices. For example, a communication protocol may include a frequency that communications are to be sent at, one or more rules for decoding communications, one or more rules for encoding communications, encryption rules, or any combination thereof.

In some examples, communication protocols 72 may include one or more communication protocols for acoustic communication via acoustic circuitry 63. The one or more communication protocols for acoustic communication may include rules, standards, or parameters for receiving acoustic singles via acoustic receiving circuitry 64 and/or sending one or more acoustic signals via acoustic transmission circuitry 66. For example, communication protocols 72 may include one or more rules for decoding acoustic communication signals received via acoustic receiving circuitry 64.

In some examples, memory 52 is configured to store collected data 74. Collected data 74 may include any data sensed, processed, or analyzed by ICD 9, where the data is acquired via any combination of electrodes 48, sensor(s) 58, communication circuitry 60, and acoustic receiving circuitry 64. In some examples, collected data 74 includes a cardiac EGM recording sensed by sensing circuitry 54 via electrodes 48 and processed by processing circuitry 50. Collected data 74 may additionally or alternatively include data acquired by one or more chemical sensors of sensor(s) 58, acoustic physiological data collected by acoustic receiving circuitry 64, motion data collected by one or more accelerometers of sensor(s) 58, temperature data, or any combination thereof. In some examples, collected data 74 w is indicative of a presence of or a possibility of at least one heart condition (e.g., heart failure). In general, collected data 74 may represent physiological signals acquired from patient 12 over a period of time. In some examples, the period of time lasts for greater than 12 hours and less than 72 hours. In other examples, the period of time lasts for up to one month. Put another way, ICD 9 is configured to continuously monitor physiological signals over the period of time and store at least some of these physiological signals in memory 52 as collected data 74.

In some examples, memory 52 is configured to store operational parameters 76. Operational parameters 76 may govern aspects of the operation of ICD 9. For example, operational parameters 76 may include combinations of electrodes 48 and sensor(s) 58 for sensing physiological signals of patient 12. Additionally, or alternatively, operational parameters 76 may include a sampling rate for sampling analog signals sensed by electrodes 48 and sensor(s) 58. Operational parameters 76 may be updated based on instructions received from an external device (e.g., external device 11) via communication circuitry 60. In some examples, processing circuitry 50 of ICD 9 updates operational parameters 76 only if instructions to update operational parameters 76 are received over a secure link.

Processing circuitry 50 may in some examples, be configured to receive, via the acoustic receiving circuitry 64 from an external device 11, a sequence of acoustic communication signals that are separate from one or more acoustic biometric signals. In some examples, the sequence of acoustic communication signals may comprise a sequence of acoustic pulses. Acoustic receiving circuitry 64 may generate a signal (e.g., an electrical signal) that indicates an occurrence of each acoustic pulse of the sequence of acoustic pulses at the time that acoustic receiving circuitry 64 receives each acoustic pulse. In some examples, the signal generated by acoustic receiving circuitry 64 may indicate a magnitude of each acoustic pulse received by acoustic receiving circuitry 64. In some examples, louder acoustic pulses received by acoustic receiving circuitry 64 may cause acoustic receiving circuitry 64 to indicate a greater magnitude and quieter acoustic pulses received by acoustic receiving circuitry 64 may cause acoustic receiving circuitry 64 to indicate a smaller magnitude.

Processing circuitry 50 is configured to decode the sequence of acoustic communication signals received by acoustic receiving circuitry 64 to identify one or more requested actions. Communication protocols 72 may include one or more rules for decoding the sequence of acoustic communication signals received by acoustic receiving circuitry 64. For example, the rules may include a mapping of parameters to messages such that processing circuitry 50 may decode the sequence of acoustic communication signals received by acoustic receiving circuitry 64 to identify the one or more requested actions. In some examples, the one or more requested actions include a request to establish a communication link via communication circuitry 60. In some examples, the one or more requested actions include a request to establish a communication link via communication circuitry 60. In some examples, the one or more requested actions include a request for information. In some examples, the one or more requested actions include a request to update one or more parameters of ICD 9. Processing circuitry 50 may control ICD 9 to perform the one or more requested actions.

Communication circuitry 60 may be configured for wireless communication according to a communication protocol of communication protocols 72. In some examples, to decode a sequence of acoustic communication signals received by acoustic receiving circuitry 64, processing circuitry 50 is configured to determine that the sequence of acoustic communication signals comprises a request to establish a communication link between ICD 9 and external device 11. Processing circuitry 50 may transition the communication circuitry 60 from operating at a low-power mode to operating at a high-power mode to enable communication according to the communication protocol.

The term "low-power mode" may be used herein to refer to an operational mode of communication circuitry 60 where communication circuitry 60 is not capable of communicating according to the communication protocol. In some examples, to communicate according to the communication protocol, communication circuitry 60 must draw more than a threshold amount of power from power source 70. When communication circuitry 60 is operating in the low-power mode, communication circuitry 60 may draw lower than the threshold amount of power from power source 70, meaning that communication circuitry 60 cannot communicate according to the communication protocol. The term "high-power mode" may be used herein to refer to an operational mode of communication circuitry 60 where communication circuitry 60 is capable of communicating according to the communication protocol. When communication circuitry 60 is operating in the high-power mode, communication circuitry 60 may draw greater than the threshold amount of power from power source 70, meaning that communication circuitry 60 can communicate according to the communication protocol.

Processing circuitry 50 may establish the communication link between ICD 9 and the external device 11 according to the communication protocol based on transitioning the communication circuitry 60 from the low-power mode to the high-power mode. In some examples, establishing the communication link may include one or more security steps, such as encrypting the communication link. In some examples, the communication link might not be encrypted. The communication link may be according to a communication protocol of communication protocols 72. In some examples, the communication protocol is according to a Bluetooth® communication protocol for communicating via a Bluetooth® radio of communication circuitry 60. This means that processing circuitry 50 may establish the communication link between ICD 9 and the external device 11 according to the communication protocol via communication circuitry 60 based on receiving the sequence of acoustic communication signals via acoustic receiving circuitry 64 separate from communication circuitry 60. In other words, processing circuitry 50 may activate communication circuitry 60 based on receiving a request from external device

11, but processing circuitry 50 may receive the request to activate communication circuitry 60 via a communication channel that does not use communication circuitry 60, because communication circuitry 60 might not be capable of communication while operating in the low-power mode.

In some examples, processing circuitry 50 may be configured to receive, via the communication link between ICD 9 and external device 11, a request to terminate the communication link. Processing circuitry 50 may transition the communication circuitry 60 from operating at the high-power mode to operating at the low-power mode in response to receiving the request to terminate the communication link. That is, processing circuitry 50 may transition the communication circuitry 60 to an operating mode that does not draw enough power for communication according to the communication protocol of the communication link. In some examples, processing circuitry 50 may terminate the communication link without receiving a message. Transitioning the communication circuitry 60 from operating at the high-power mode to operating at the low-power mode may decrease an amount of power that communication circuitry 60 draws from power source 70, and thus preserve a longevity of power source 70.

Processing circuitry 50 may in some examples, determine that a sequence of acoustic communication signals received by acoustic receiving circuitry 64 includes a request to provide status information corresponding to ICD 9. In some examples, ICD 9 may receive the request to provide status information in an event that a communication link via communication circuitry 60 (e.g., a Bluetooth® communication link) is offline. The request to provide status information may thus comprise a request to provide status information via an alternative communication channel.

In response to receiving the sequence of acoustic communication signals comprising the request to provide status information from external device 11, processing circuitry 50 is configured to control the acoustic transmission circuitry 66 to generate a sequence of acoustic communication signals for output to external device 11 that includes the status information corresponding to ICD 9. In other words, processing circuitry 50 may provide the status information using acoustic communication and without using communication circuitry 60. This means that ICD 9 may communicate with external device 11 when communication via communication circuitry 60 is offline for any reason, and acoustic circuitry 63 provide ICD 9 with an alternative channel of communication.

In some examples, processing circuitry 50 may determine that a sequence of acoustic communication signals received by acoustic receiving circuitry 64 includes a request to update one or more parameters of the ICD 9. Processing circuitry 50 may update, based on the request to update one or more parameters of ICD 9, the one or more parameters of ICD 9. In some examples, the request to update the one or more parameters of the ICD 9 comprises a request to implement a therapy mode (e.g., an emergency VVI pacing mode), and processing circuitry 50 is configured to implement the therapy mode based on the request to implement the therapy mode. In some examples, the request to update the one or more parameters of the ICD 9 comprises a request to operate one or more of operational parameters 76.

Figure 3:
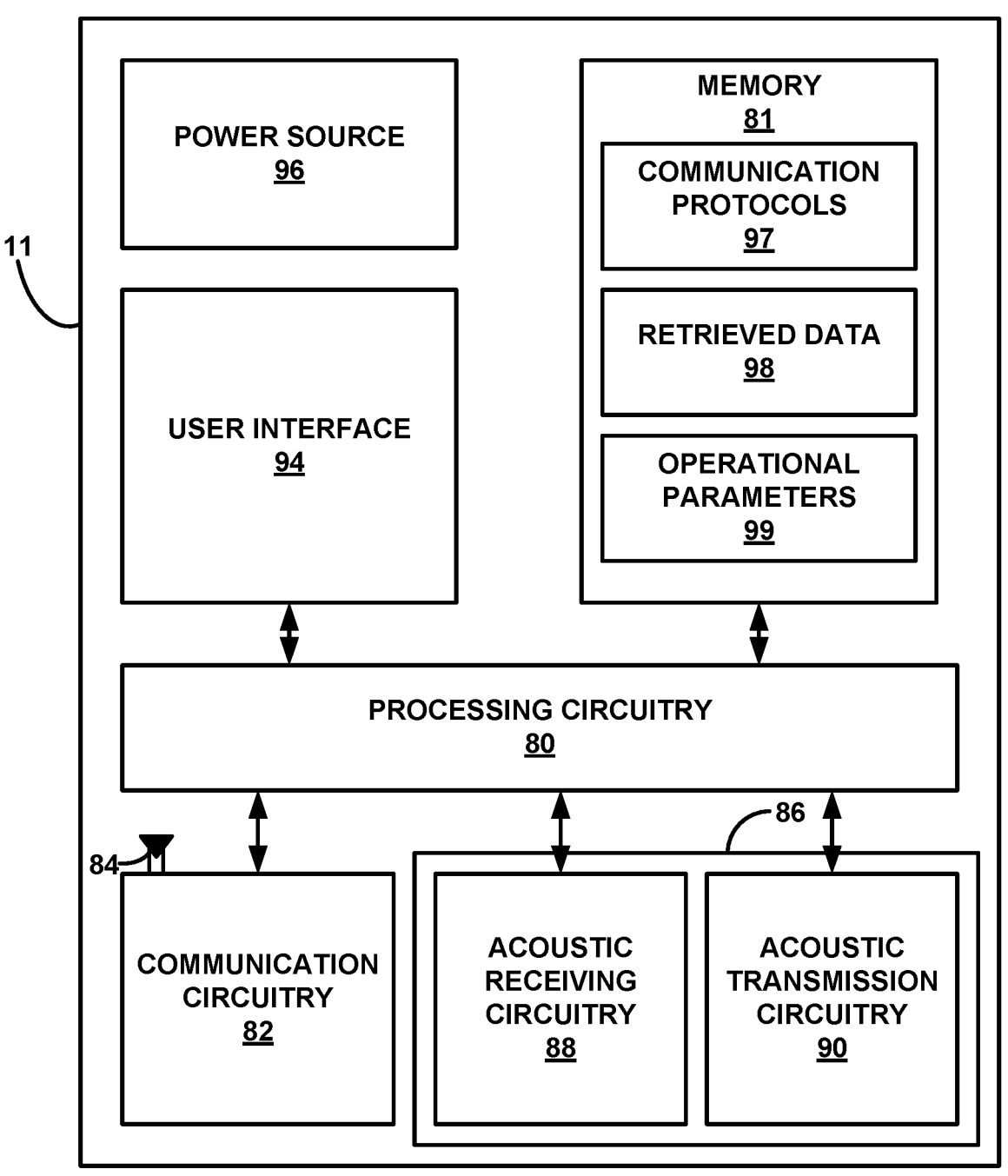
FIG. 3 is a block diagram illustrating an example configuration of components of an external device, in accordance with one or more techniques of this disclosure.

FIG. 3 is a block diagram illustrating an example configuration of components of external device 11 in accordance with one or more techniques of this disclosure. In the example of FIG. 3, external device 11 includes processing circuitry 80, memory 81, communication circuitry 82, antenna 84, acoustic circuitry 86 including acoustic receiving circuitry 88 and acoustic transmission circuitry 90, user interface 94, and power source 96. Memory 81 is configured to store communication protocols 97, retrieved data 98, and operational parameters 99.

Processing circuitry 80, in one example, may include one or more processors that are configured to implement functionality and/or process instructions for execution within external device 11. For example, processing circuitry 80 may be capable of processing instructions stored in memory 81. Processing circuitry 80 may include, for example, microprocessors, DSPs, ASICs, FPGAs, or equivalent discrete or integrated logic circuitry, or a combination of any of the foregoing devices or circuitry. Accordingly, processing circuitry 80 may include any suitable structure, whether in hardware, software, firmware, or any combination thereof, to perform the functions ascribed herein to processing circuitry 80.

Memory 81 may be configured to store information within external device 11 during operation. Memory 81 may include a computer-readable storage medium or computer-readable storage device. In some examples, memory 81 includes one or more of a short-term memory or a long-term memory. Memory 81 may include, for example, RAM, DRAM, SRAM, magnetic discs, optical discs, flash memories, or forms of EPROM or EEPROM. In some examples, memory 81 is used to store data indicative of instructions for execution by processing circuitry 80. Memory 81 may be used by software or applications running on external device 11 to temporarily store information during program execution.

Communication circuitry 82 may include any suitable hardware, firmware, software, or any combination thereof for communicating with another device, such as ICD 9. Under the control of processing circuitry 80, communication circuitry 82 may receive downlink telemetry from, as well as send uplink telemetry to ICD 9 or another device. In some examples, communication circuitry 82 includes a first set of communication circuitry configured for transmitting and receiving signals according to a communication protocol developed by the manufacturer of ICD 9 or a third-party developer. In some examples, communication circuitry 82 further includes a second set of communication circuitry which defines a Bluetooth® radio configured for transmitting and receiving signals according to Bluetooth® communication protocols. However, communication circuitry 82 does not necessarily include separate sets of circuitry corresponding to different communication protocols. In some examples, communication circuitry 82 includes a single set of circuitry configured for transmitting and receiving signals according to a plurality of communication protocols. In some examples, communication circuitry 82 includes a single set of circuitry configured for transmitting and receiving signals according to one or more Bluetooth® communication protocols without including circuitry for transmitting and receiving signals according to other communication protocols.

In some examples, communication circuitry 82 includes any one or combination of a Bluetooth® radio, an electronic oscillator, frequency modulation circuitry, frequency demodulation circuitry, amplifier circuitry, and power switches such as a MOSFET, a BJT, an IGBT, a JFET, or another element that uses voltage for its control.

Acoustic circuitry 86 may include acoustic receiving circuitry 88 configured to receive one or more acoustic signals. Acoustic receiving circuitry 88 may include one or more acoustic sensors configured to generate one or more electrical signals based on receiving one or more acoustic signals. For example, acoustic sensors of acoustic receiving circuitry 88 receive one or more acoustic signals, the acoustic sensors may generate an electrical signal that indicates one or more parameters of the received acoustic signals. For example, the electrical signal generated by the acoustic sensors may indicate a magnitude of one or more received acoustic signals, a duration of one or more received acoustic signals, a frequency of one or more received acoustic signals, or any combination thereof.

In some examples, acoustic receiving circuitry 88 may be configured to sense one or more acoustic communication signals. The one or more acoustic communication signals may represent acoustic communication signals emitted by another device to communicate with external device 11. For example, ICD 9 or another device may emit one or more acoustic communication signals and acoustic receiving circuitry 88 may sense the one or more acoustic communication signals. One or more acoustic sensors of acoustic receiving circuitry 88 may generate one or more electrical signals that indicate the one or more acoustic communication signals.

Acoustic receiving circuitry 88 may in some examples, receive a sequence of acoustic communication signals. In some examples, the sequence of acoustic communication signals may include one or more instructions or requests. In some examples, the sequence of acoustic communication signals may include information, for example, a sequence of acoustic communication signals may include information from ICD 9 in response to a request sent by external device 11. Processing circuitry 80 may decode the sequence of acoustic communication signals in order to identify the information.

Acoustic circuitry 86 may include acoustic transmission circuitry 90. In some examples, acoustic transmission circuitry 90 may be configured to generate one or more acoustic signals for output from ICD 9. For example, acoustic transmission circuitry 90 may include one or more piezoelectric transducers or one or more other components configured to generate acoustic signals. Processing circuitry 80 may be configured to control acoustic transmission circuitry 90 to generate one or more acoustic signals for output that are separate from one or more acoustic transmission circuitry received by acoustic receiving circuitry 88. In some examples, processing circuitry 80 may control acoustic transmission circuitry 90 to generate acoustic signals that include information. In some examples, processing circuitry 80 may control acoustic transmission circuitry 90 to generate acoustic signals that include a request for ICD 9 to establish a communication link. In some examples, processing circuitry 80 may control acoustic transmission circuitry 90 to generate acoustic signals that include a request for ICD 9 to provide status information. In some examples, processing circuitry 80 may control acoustic transmission circuitry 90 to generate acoustic signals that include a request for ICD 9 to update one or more parameters. In some examples, acoustic receiving circuitry 88 and acoustic transmission circuitry 90 may share circuitry and/or one or more other components. For example, a piezoelectric transducer may be configured to both sense audio signals and generate audio signals.

A user, such as a clinician or patient 12, may interact with external device 11 through user interface 94. User interface 94 includes a display (not shown), such as an LCD or LED display or other type of screen, with which processing circuitry 80 may present information related to ICD 9 (e.g., EGM signals obtained from at least one electrode or at least one electrode combination). In addition, user interface 94 may include an input mechanism to receive input from the user. The input mechanisms may include, for example, any one or more of buttons, a keypad (e.g., an alphanumeric keypad), a peripheral pointing device, a touch screen, or another input mechanism that allows the user to navigate through user interfaces presented by processing circuitry 80 of external device 11 and provide input. In other examples, user interface 94 also includes audio circuitry for providing audible notifications, instructions, or other sounds to patient 12, receiving voice commands from patient 12, or both. Memory 81 may include instructions for operating user interface 94 and for managing power source 96.

Power source 96 is configured to deliver operating power to the components of external device 11. Power source 96 may include a battery and a power generation circuit to produce the operating power. In some examples, the battery is rechargeable to allow extended operation. Recharging may be accomplished by electrically coupling power source 96 to a cradle or plug that is connected to an alternating current (AC) outlet. In addition, recharging may be accomplished through proximal inductive interaction between an external charger and an inductive charging coil within external device 11. In other examples, traditional batteries (e.g., nickel cadmium or lithium-ion batteries) may be used. In addition, external device 11 may be directly coupled to an alternating current outlet to operate.

External device 11 may exchange information with other devices via communication circuitry 82 according to one or more communication protocols 97. Communication protocols 97, stored in memory 81, may include sets of computer-readable instructions that determine how data is transmitted and processed. Communication protocols 97 may include one or more communication protocols that are additionally included in communication protocols 72. In other words, ICD 9 and external device 11 may be configured to exchange information according to at least one common communication protocol. In some examples, the one or more common communication protocols include at least one Bluetooth® communication protocol. Additionally, or alternatively, communication protocols 97 may include a set of communication protocols that are not available to ICD 9. In some examples, external device 11 is a consumer electronics device, such as a smartphone, a tablet, or a laptop computer. In some such examples, external device 11 may not be configured with communication protocols developed by the manufacturer of ICD 9.

Data exchanged between external device 11 and ICD 9 may include any of operational parameters 99 stored in memory 81. External device 11 may transmit data including computer readable instructions which, when implemented by ICD 9, may control ICD 9 to change one or more operational parameters according to operational parameters 99 and/or export collected data. For example, processing circuitry 80 may transmit an instruction to ICD 9 which requests ICD 9 to export collected data (e.g., a portion of collected data 74) to external device 11. In turn, external device 11 may receive the collected data from ICD 9 and store the collected data in memory 81 (e.g., as retrieved data 98). Additionally, or alternatively, processing circuitry 80 may export instructions to ICD 9 requesting ICD 9 to update electrode combinations for stimulation or sensing according to operational parameters 99.

Figure 4:
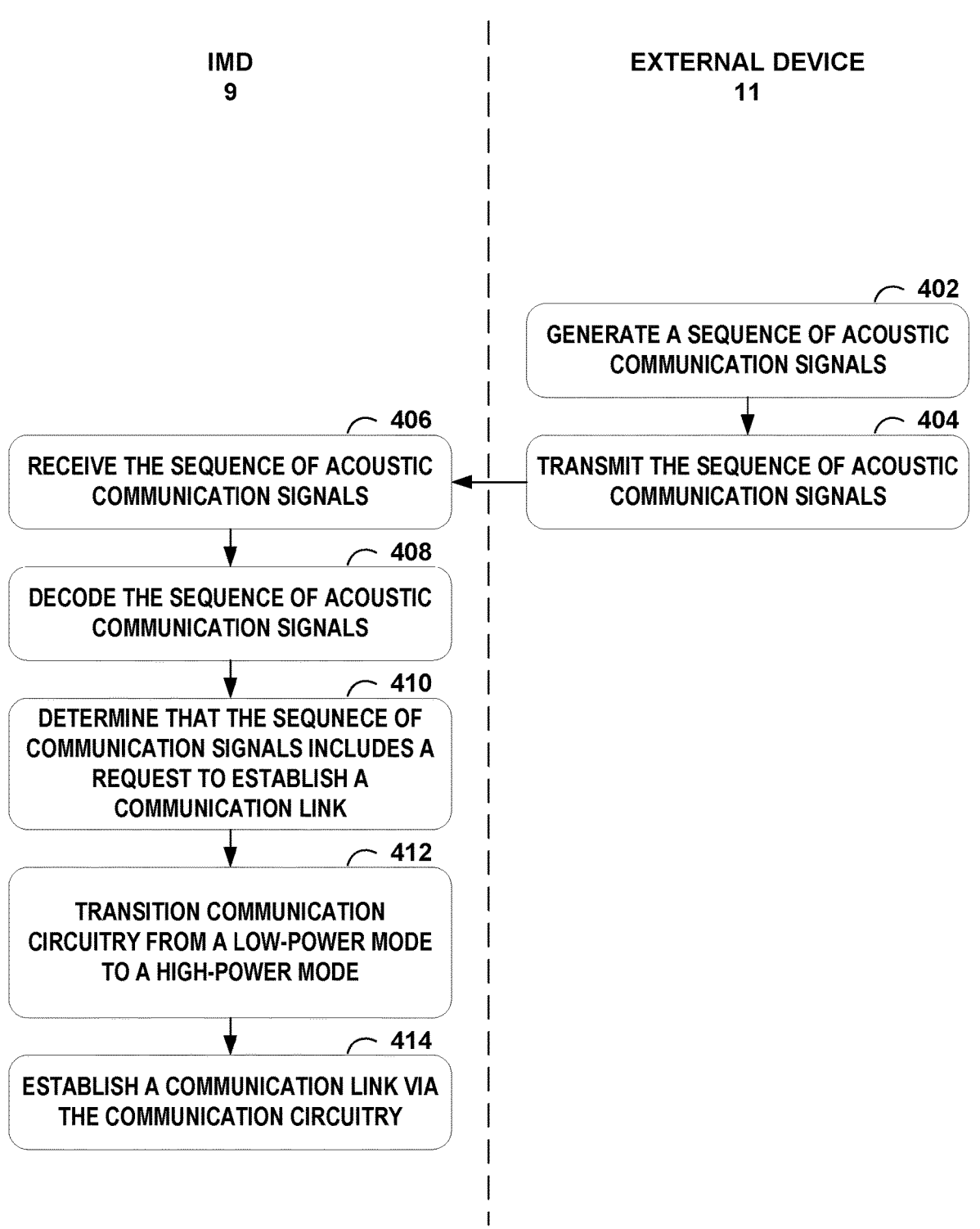
FIG. 4 is a flow diagram illustrating an example operation for establishing a communication link in response to receiving acoustic communication, in accordance with one or more techniques of this disclosure.

FIG. 4 is a flow diagram illustrating an example operation for establishing a communication link in response to receiving acoustic communication, in accordance with one or more techniques of this disclosure. The example operation is described with respect to ICD 9 and external device 11 of FIGS. 1-3, and components thereof. However, the techniques of FIG. 4 may be performed by different components of ICD 9, external device 11, or by additional or alternative medical device systems.

External device 11 may generate a sequence of acoustic communication signals (402). In some examples, the sequence of acoustic communication signals may include information. Information may include an instruction, a request, or any other information that can be encoded into the sequence of acoustic communication signals. External device 11 may transmit the sequence of acoustic communication signals (404) to ICD 9 via acoustic transmission circuitry 90. ICD 9 may receive the sequence of acoustic communication signals from external device 11 via acoustic receiving circuitry 64 of ICD 9 (406).

Processing circuitry 50 of ICD 9 is configured to decode the sequence of acoustic communication signals (408). In some examples, processing circuitry 50 may decode the sequence of acoustic communication signals based on one or more communication protocols 72 stored in memory 52. Based on decoding the sequence of acoustic communication signals, processing circuitry 50 may determine that the sequence of acoustic communication signals includes a request to establish a communication link (410). In some examples, the request may represent a request to establish the communication link via communication circuitry 60 according to a communication protocol. The communication protocol may in some examples, be a Bluetooth® communication protocol.

Processing circuitry 50 may transition communication circuitry 60 from a low-power mode to a high-power mode based on determining that the sequence of acoustic communication signals includes a request to establish a communication link (412). In some examples, the processing circuitry 50 transitions communication circuitry 60 from a low-power mode to a high-power mode to allow communication circuitry 60 to communicate according to the communication protocol. ICD 9 may establish a communication link via the communication circuitry 60 (414). Establishing the communication link may include sending one or more advertisements. In some examples, the communication link may represent a communication link between ICD 9 and external device 11. In some examples, External device 11 may send and/or receive one or more messages over the communication link via communication circuitry 82 and ICD 9 may send and/or receive one or more messages over the communication link via communication circuitry 60.

Figure 5:
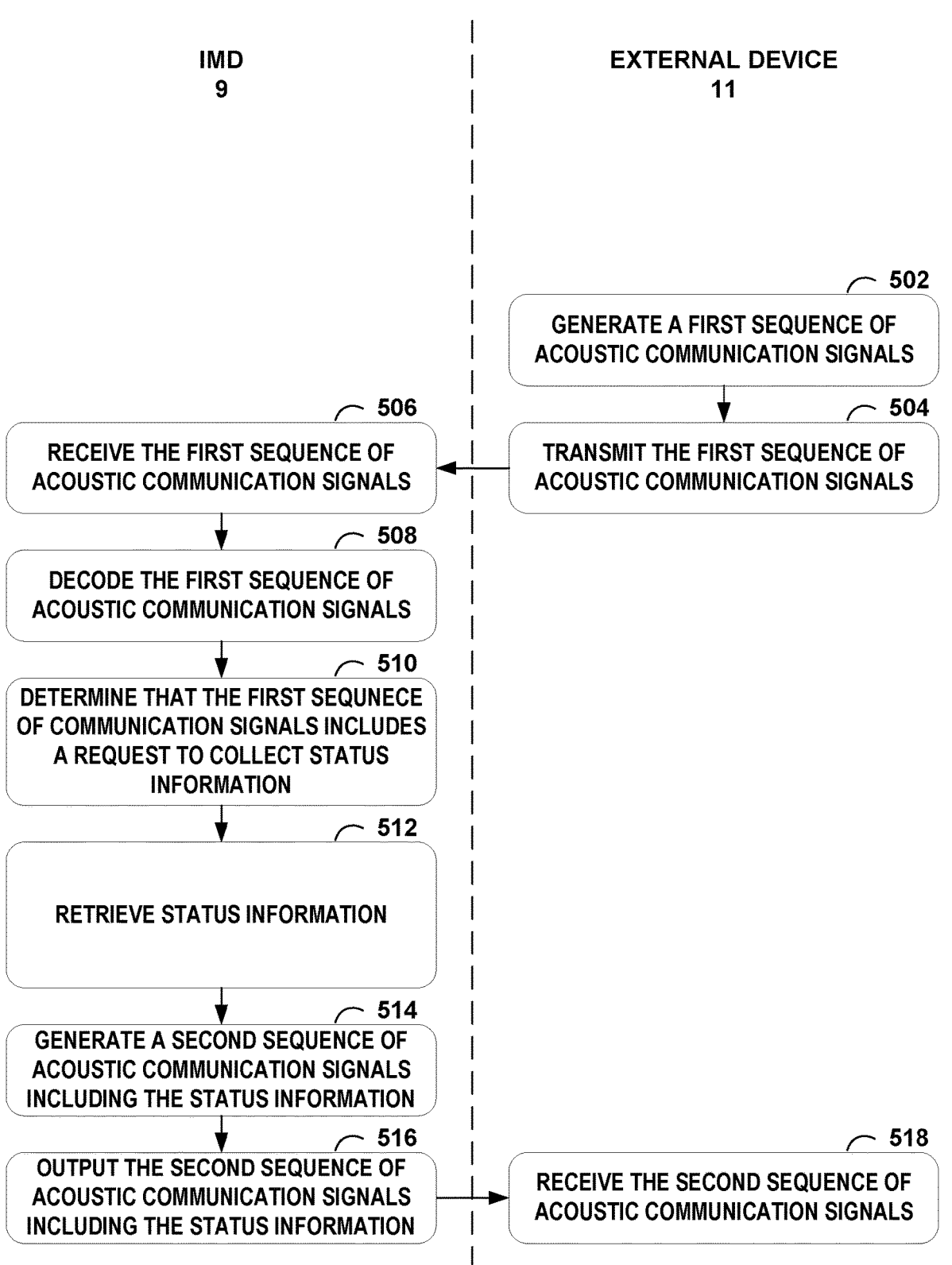
FIG. 5 is a flow diagram illustrating an example operation for requesting information from an implantable medical device, in accordance with one or more techniques of this disclosure.

FIG. 5 is a flow diagram illustrating an example operation for requesting information from an implantable medical device, in accordance with one or more techniques of this disclosure. The example operation is described with respect to ICD 9 and external device 11 of FIGS. 1-3, and components thereof. However, the techniques of FIG. 5 may be performed by different components of ICD 9, external device 11, or by additional or alternative medical device systems.

External device 11 may generate a first sequence of acoustic communication signals (502). In some examples, the first sequence of acoustic communication signals may include information. Information may include an instruction, a request, or any other information that can be encoded into the sequence of acoustic communication signals. External device 11 may transmit the first sequence of acoustic communication signals (504) to ICD 9 via acoustic transmission circuitry 90. ICD 9 may receive the first sequence of acoustic communication signals from external device 11 via acoustic receiving circuitry 64 of ICD 9 (506).

Processing circuitry 50 of ICD 9 is configured to decode the first sequence of acoustic communication signals (508). In some examples, processing circuitry 50 may decode the first sequence of acoustic communication signals based on one or more communication protocols 72 stored in memory 52. Based on decoding the first sequence of acoustic communication signals, processing circuitry 50 may determine that the first sequence of acoustic communication signals include a request to collect status information (510). Processing circuitry 50 may retrieve the status information (512). Processing circuitry 50 may control acoustic transmission circuitry 66 to generate a second sequence of acoustic communication signals including the status information (514). Acoustic transmission circuitry 66 may output the second sequence of acoustic communication signals including the status information (516). External device 11 may receive the second sequence of acoustic communication signals via acoustic receiving circuitry 88 (518).

FIG. 6 is a flow diagram illustrating an example operation for updating one or more parameters, in accordance with one or more techniques of this disclosure. The example operation is described with respect to ICD 9 and external device 11 of FIGS. 1-3, and components thereof. However, the techniques of FIG. 6 may be performed by different components of ICD 9, external device 11, or by additional or alternative medical device systems.

External device 11 may generate a sequence of acoustic communication signals (602). In some examples, the sequence of acoustic communication signals may include information. Information may include an instruction, a request, or any other information that can be encoded into the sequence of acoustic communication signals. External device 11 may transmit the sequence of acoustic communication signals (604) to ICD 9 via acoustic transmission circuitry 90. ICD 9 may receive the sequence of acoustic communication signals from external device 11 via acoustic receiving circuitry 64 of ICD 9 (606).

Processing circuitry 50 of ICD 9 is configured to decode the sequence of acoustic communication signals (608). In some examples, processing circuitry 50 may decode the sequence of acoustic communication signals based on one or more communication protocols 72 stored in memory 52. Based on decoding the sequence of acoustic communication signals, processing circuitry 50 may determine that the sequence of acoustic communication signals includes a request to update one or more parameters of the ICD 9 (610). Processing circuitry 50 may update the one or more parameters of ICD 9 (612). Processing circuitry 50 may output, via acoustic transmission circuitry 66, a message indicating that the one or more parameters are updated (614). Processing circuitry 50 may receive, via acoustic receiving circuitry 88, the message indicating that the one or more parameters are updated (616).

The following examples are a non-limiting list of clauses in accordance with one or more techniques of this disclosure.

Clause 1. A medical device system includes an IMD configured to be implanted underneath a skin of a patient, the IMD comprising: acoustic receiving circuitry configured to: receive one or more acoustic communication signals; and receive one or more acoustic biometric signals from the patient. The IMD also includes communication circuitry configured for wireless communication according to a communication protocol. The medical device system also includes processing circuitry configured to: receive, via the acoustic receiving circuitry, a sequence of acoustic communication signals of the one or more acoustic communication signals that are separate from the one or more acoustic biometric signals; decode the sequence of acoustic communication signals to identify one or more requested actions; and control the IMD to perform the one or more requested actions.

Clause 2. The medical device system of clause 1, wherein the IMD further comprises: communication circuitry configured for wireless communication according to a communication protocol, and wherein to decode the sequence of acoustic communication signals, the processing circuitry is configured to determine that the sequence of acoustic communication signals comprise a request to establish a communication link between the IMD and one or more other devices. The processing circuitry is configured to: transition the communication circuitry from operating at a low-power mode to operating at a high-power mode to enable communication according to the communication protocol; and establish the communication link between the IMD and the one or more other devices according to the communication protocol.

Clause 3. The medical device system of clause 2, wherein the processing circuitry is further configured to: receive, via the communication link, a request to terminate the communication link; and transition the communication circuitry from operating at the high-power mode to operating at the low-power mode.

Clause 4. The medical device system of any of clauses 1-3, wherein the sequence of acoustic communication signals comprises a first sequence of acoustic communication signals, and wherein the IMD further comprises acoustic transmission circuitry configured to generate one or more acoustic signals for output that are separate from the first sequence of acoustic communication signals.

Clause 5. The medical device system of clause 4, wherein to decode the first sequence of acoustic communication signals, the processing circuitry is further configured to: determine that the first sequence of acoustic communication signals comprises a request to provide status information corresponding to the IMD, and wherein the processing circuitry is further configured to control the acoustic transmission circuitry to generate a second sequence of acoustic communication signals for output to the external device, wherein the second sequence of acoustic communication signals comprises the status information corresponding to the IMD.

Clause 6. The medical device system of any of clauses 4-5, wherein to decode the sequence of acoustic communication signals, the processing circuitry is further configured to: determine that the sequence of acoustic communication signals comprises a request to update one or more parameters of the IMD, and wherein the processing circuitry is further configured to update, based on the request to update one or more parameters of the IMD, the one or more parameters of the IMD.

Clause 7. The medical device system of clause 6, wherein the request to update the one or more parameters of the IMD comprises a request to implement a therapy mode, and wherein the processing circuitry is configured to implement the therapy mode based on the request to implement the therapy mode.

Clause 8. The medical device system of any of clauses 1-7, wherein the processing circuitry is further configured to: receive, via the acoustic receiving circuitry, a set of acoustic biometric signals that are separate from the one or more acoustic communication signals; and process the set of acoustic biometric signals in order to monitor one or more patient conditions.

Clause 9. The medical device system of clause 8, wherein the set of acoustic biometric signals comprise heart sounds from a heart of the patient, and wherein the processing circuitry is configured to process the heart sounds of the patient in order to determine whether a heart failure condition of the patient is worsening.

Clause 10. The medical device system of any of clauses 1-9, wherein the IMD further comprises stimulation generation circuitry configured to generate one or more stimulation pulses for delivery to the patient via one or more electrodes, and wherein the processing circuitry is further configured to: determine, based on the one or more acoustic biometric signals from the patient, one or more stimulation parameters; and control the stimulation generation circuitry to deliver one or more stimulation pulses to the patient via the one or more electrodes according to the one or more stimulation parameters.

Clause 11. The medical device system of any of clauses 1-10, wherein the IMD comprises an ICD.

Clause 12. The medical device system of any of clauses 1-11, further comprising an external device configured to send the sequence of acoustic communication signals to the IMD.

Clause 13. A method comprising: receiving, by processing circuitry via acoustic receiving circuitry, a sequence of acoustic communication signals of one or more acoustic communication signals that are separate from one or more acoustic biometric signals, wherein an IMD configured to be implanted underneath a skin of a patient comprises the acoustic receiving circuitry configured to receive the one or more acoustic communication signals and receive the one or more acoustic biometric signals from the patient, and wherein the IMD comprises communication circuitry configured for wireless communication according to a communication protocol. The method also comprises decoding, by the processing circuitry, the sequence of acoustic communication signals to identify one or more requested actions; and controlling, by the processing circuitry, the IMD to perform the one or more requested actions.

Clause 14. The method of clause 13, wherein the IMD further comprises communication circuitry configured for wireless communication according to a communication protocol, wherein decoding the sequence of acoustic communication signals comprises determining that the sequence of acoustic communication signals comprise a request to establish a communication link between the IMD and one or more other devices, and wherein the method further comprises: transitioning, by the processing circuitry, the communication circuitry from operating at a low-power mode to operating at a high-power mode to enable communication according to the communication protocol; and establishing, by the communication circuitry, the communication link between the IMD and the one or more other devices according to the communication protocol.

Clause 15. The method of clause 14, wherein the method further comprises: receiving, by the processing circuitry via the communication link, a request to terminate the communication link; and transitioning, by the processing circuitry, the communication circuitry from operating at the high-power mode to operating at the low-power mode.

Clause 16. The method of any of clauses 13-15, wherein the sequence of acoustic communication signals comprises a first sequence of acoustic communication signals, and wherein the IMD further comprises acoustic transmission circuitry configured to generate one or more acoustic signals for output that are separate from the first sequence of acoustic communication signals.

Clause 17. The method of clause 16, wherein decoding the first sequence of acoustic communication signals comprises: determining that the first sequence of acoustic communication signals comprises a request to provide status information corresponding to the IMD, and wherein the method further comprises controlling, by the processing circuitry, the acoustic transmission circuitry to generate a second sequence of acoustic communication signals for output to the external device, wherein the second sequence of acoustic communication signals comprises the status information corresponding to the IMD.

Clause 18. The method of any of clauses 16-17, wherein decoding the sequence of acoustic communication signals comprises: determining that the sequence of acoustic communication signals comprises a request to update one or more parameters of the IMD, and wherein the method further comprises updating, by the processing circuitry based on the request to update one or more parameters of the IMD, the one or more parameters of the IMD.

Clause 19. The method of clause 18, wherein the request to update the one or more parameters of the IMD comprises a request to implement a therapy mode, and wherein the method further comprises implementing, by the processing circuitry, the therapy mode based on the request to implement the therapy mode.

Clause 20. A non-transitory computer-readable medium includes instructions for causing one or more processors to: receive, via acoustic receiving circuitry, a sequence of acoustic communication signals of one or more acoustic communication signals that are separate from one or more acoustic biometric signals, wherein an IMD configured to be implanted underneath a skin of a patient comprises the acoustic receiving circuitry configured to receive the one or more acoustic communication signals and receive the one or more acoustic biometric signals from the patient, and wherein the IMD comprises communication circuitry configured for wireless communication according to a communication protocol. The instructions also cause the one or more processors to decode the sequence of acoustic communication signals to identify one or more requested actions; and control the IMD to perform the one or more requested actions.

The techniques described in this disclosure may be implemented, at least in part, in hardware, software, firmware, or any combination thereof. For example, various aspects of the techniques may be implemented within one or more microprocessors, DSPs, ASICs, FPGAs, or any other equivalent integrated or discrete logic QRS circuitry, as well as any combinations of such components, embodied in external devices, such as physician or patient programmers, stimulators, or other devices. The terms "processor" and "processing circuitry" may generally refer to any of the foregoing logic circuitry, alone or in combination with other logic circuitry, or any other equivalent circuitry, and alone or in combination with other digital or analog circuitry.

For aspects implemented in software, at least some of the functionality ascribed to the systems and devices described in this disclosure may be embodied as instructions on a computer-readable storage medium such as RAM, DRAM, SRAM, magnetic discs, optical discs, flash memories, or forms of EPROM or EEPROM. The instructions may be executed to support one or more aspects of the functionality described in this disclosure.

In addition, in some aspects, the functionality described herein may be provided within dedicated hardware and/or software modules. Depiction of different features as modules or units is intended to highlight different functional aspects and does not necessarily imply that such modules or units must be realized by separate hardware or software components. Rather, functionality associated with one or more modules or units may be performed by separate hardware or software components or integrated within common or separate hardware or software components. Also, the techniques could be fully implemented in one or more circuits or logic elements. The techniques of this disclosure may be implemented in a wide variety of devices or apparatuses, including an IMD, an external programmer, a combination of an IMD and external programmer, an integrated circuit (IC) or a set of ICs, and/or discrete electrical circuitry, residing in an IMD and/or external programmer.

What is claimed is:

1. A medical device system comprising:
an implantable medical device (IMD) configured to be implanted underneath a skin of a patient, the IMD comprising:
    acoustic receiving circuitry configured to:
        receive one or more acoustic communication signals; and
        receive one or more acoustic biometric signals from the patient, the one or more acoustic biometric signals representing sounds caused by physiological functions of the patient; and
    communication circuitry configured for wireless communication according to a communication protocol; and
processing circuitry configured to:
    receive, via the acoustic receiving circuitry, a sequence of acoustic communication signals of the one or more acoustic communication signals that are separate from the one or more acoustic biometric signals;
    decode the sequence of acoustic communication signals to identify one or more requested actions; and
    control the IMD to perform the one or more requested actions.

2. The medical device system of claim 1,
wherein to decode the sequence of acoustic communication signals, the processing circuitry is configured to determine that the sequence of acoustic communication signals comprise a request to establish a communication link between the IMD and one or more other devices, and
wherein the processing circuitry is configured to:
    transition the communication circuitry from operating at a low-power mode to operating at a high-power mode to enable communication according to the communication protocol; and
    establish the communication link between the IMD and the one or more other devices according to the communication protocol.

3. The medical device system of claim 2, wherein the processing circuitry is further configured to:
    receive, via the communication link, a request to terminate the communication link; and
    transition the communication circuitry from operating at the high-power mode to operating at the low-power mode.

4. The medical device system of claim 1, wherein the sequence of acoustic communication signals comprises a first sequence of acoustic communication signals, and wherein the IMD further comprises acoustic transmission circuitry configured to generate one or more acoustic signals for output that are separate from the first sequence of acoustic communication signals.

5. The medical device system of claim 4, wherein to decode the first sequence of acoustic communication signals, the processing circuitry is further configured to:
    determine that the first sequence of acoustic communication signals comprises a request to provide status information corresponding to the IMD, and
    wherein the processing circuitry is further configured to control the acoustic transmission circuitry to generate a second sequence of acoustic communication signals for output, wherein the second sequence of acoustic communication signals comprises the status information corresponding to the IMD.

6. The medical device system of claim 1, wherein to decode the sequence of acoustic communication signals, the processing circuitry is further configured to:
    determine that the sequence of acoustic communication signals comprises a request to update one or more parameters of the IMD, and
    wherein the processing circuitry is further configured to update, based on the request to update one or more parameters of the IMD, the one or more parameters of the IMD.

7. The medical device system of claim 6, wherein the request to update the one or more parameters of the IMD comprises a request to implement a therapy mode, and wherein the processing circuitry is configured to implement the therapy mode based on the request to implement the therapy mode.

8. The medical device system of claim 1, wherein the processing circuitry is further configured to:
    receive, via the acoustic receiving circuitry, a set of acoustic biometric signals that are separate from the one or more acoustic communication signals; and
    process the set of acoustic biometric signals in order to monitor one or more patient conditions.

9. The medical device system of claim 8, wherein the set of acoustic biometric signals comprise heart sounds from a heart of the patient, and wherein the processing circuitry is configured to process the heart sounds of the patient in order to determine whether a heart failure condition of the patient is worsening.

10. The medical device system of claim 1, wherein the IMD further comprises stimulation generation circuitry configured to generate one or more stimulation pulses for delivery to the patient via one or more electrodes, and wherein the processing circuitry is further configured to:
    determine, based on the one or more acoustic biometric signals from the patient, one or more stimulation parameters; and
    control the stimulation generation circuitry to deliver one or more stimulation pulses to the patient via the one or more electrodes according to the one or more stimulation parameters.

11. The medical device system of claim 1, wherein the IMD comprises an implantable cardioverter defibrillator (ICD).

12. The medical device system of claim 1, further comprising an external device configured to send the sequence of acoustic communication signals to the IMD.

13. A method comprising:
    receiving, by processing circuitry via acoustic receiving circuitry, a sequence of acoustic communication signals of one or more acoustic communication signals that are separate from one or more acoustic biometric signals, wherein the one or more acoustic biometric signals represent sounds caused by physiological functions of a patient, wherein an implantable medical device (IMD) configured to be implanted underneath a skin of a patient comprises the acoustic receiving circuitry configured to receive the one or more acoustic communication signals and receive the one or more acoustic biometric signals from the patient, and wherein the IMD comprises communication circuitry configured for wireless communication according to a communication protocol;

decoding, by the processing circuitry, the sequence of acoustic communication signals to identify one or more requested actions; and controlling, by the processing circuitry, the IMD to perform the one or more requested actions.

14. The method of claim 13, wherein decoding the sequence of acoustic communication signals comprises determining that the sequence of acoustic communication signals comprise a request to establish a communication link between the IMD and one or more other devices, and wherein the method further comprises:

transitioning, by the processing circuitry, the communication circuitry from operating at a low-power mode to operating at a high-power mode to enable communication according to the communication protocol; and establishing, by the communication circuitry, the communication link between the IMD and the one or more other devices according to the communication protocol.

15. The method of claim 14, wherein the method further comprises:

receiving, by the processing circuitry via the communication link, a request to terminate the communication link; and transitioning, by the processing circuitry, the communication circuitry from operating at the high-power mode to operating at the low-power mode.

16. The method of claim 13, wherein the sequence of acoustic communication signals comprises a first sequence of acoustic communication signals, and wherein the IMD further comprises acoustic transmission circuitry configured to generate one or more acoustic signals for output that are separate from the first sequence of acoustic communication signals.

17. The method of claim 16, wherein decoding the first sequence of acoustic communication signals comprises:

determining that the first sequence of acoustic communication signals comprises a request to provide status information corresponding to the IMD, and wherein the method further comprises controlling, by the processing circuitry, the acoustic transmission circuitry to generate a second sequence of acoustic communication signals, wherein the second sequence of acoustic communication signals comprises the status information corresponding to the IMD.

18. The method of claim 13, wherein decoding the sequence of acoustic communication signals comprises:

determining that the sequence of acoustic communication signals comprises a request to update one or more parameters of the IMD, and wherein the method further comprises updating, by the processing circuitry based on the request to update one or more parameters of the IMD, the one or more parameters of the IMD.

19. The method of claim 18, wherein the request to update the one or more parameters of the IMD comprises a request to implement a therapy mode, and wherein the method further comprises implementing, by the processing circuitry, the therapy mode based on the request to implement the therapy mode.

20. A non-transitory computer-readable medium comprising instructions for causing one or more processors to:

receive, via acoustic receiving circuitry, a sequence of acoustic communication signals of one or more acoustic communication signals that are separate from one or more acoustic biometric signals, wherein the one or more acoustic biometric signals represent sounds caused by physiological functions of a patient wherein an implantable medical device (IMD) configured to be implanted underneath a skin of a patient comprises the acoustic receiving circuitry configured to receive the one or more acoustic communication signals and receive the one or more acoustic biometric signals from the patient, and wherein the IMD comprises communication circuitry configured for wireless communication according to a communication protocol;

decode the sequence of acoustic communication signals to identify one or more requested actions; and control the IMD to perform the one or more requested actions.

* * * * *